United States Patent
Valverde et al.

(10) Patent No.: US 10,238,584 B2
(45) Date of Patent: Mar. 26, 2019

(54) GEL-TYPE COSMETIC COMPOSITION

(71) Applicant: L'OREAL, Paris (FR)

(72) Inventors: Elodie Valverde, Paris (FR); Véronique Ferrari, Maisons-Alfort (FR); Guillaume Cassin, Villebon sur Yvette (FR); Xavier Ray, Villeconin (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/770,182

(22) PCT Filed: Feb. 25, 2014

(86) PCT No.: PCT/IB2014/059240
§ 371 (c)(1),
(2) Date: Aug. 25, 2015

(87) PCT Pub. No.: WO2014/128680
PCT Pub. Date: Aug. 28, 2014

(65) Prior Publication Data
US 2016/0000663 A1 Jan. 7, 2016

(30) Foreign Application Priority Data

Feb. 25, 2013 (FR) ..................................... 13 00432

(51) Int. Cl.
| | |
|---|---|
| A61K 8/04 | (2006.01) |
| A61K 8/26 | (2006.01) |
| A61K 8/73 | (2006.01) |
| A61K 8/81 | (2006.01) |
| A61K 8/89 | (2006.01) |
| A61K 8/92 | (2006.01) |
| A61Q 1/04 | (2006.01) |
| A61Q 19/00 | (2006.01) |
| A61K 8/87 | (2006.01) |
| A61K 8/891 | (2006.01) |
| A61K 8/895 | (2006.01) |
| A45D 40/00 | (2006.01) |
| A61K 8/19 | (2006.01) |
| A61K 8/25 | (2006.01) |
| A61K 8/29 | (2006.01) |
| A61K 8/31 | (2006.01) |
| A61K 8/34 | (2006.01) |
| A61K 8/37 | (2006.01) |
| A61K 8/49 | (2006.01) |
| A61K 8/58 | (2006.01) |
| A61K 8/85 | (2006.01) |
| A61K 8/97 | (2017.01) |
| A61Q 1/06 | (2006.01) |
| A61Q 1/10 | (2006.01) |
| A61Q 1/12 | (2006.01) |

(52) U.S. Cl.
CPC .......... *A61K 8/042* (2013.01); *A45D 40/0068* (2013.01); *A61K 8/19* (2013.01); *A61K 8/25* (2013.01); *A61K 8/26* (2013.01); *A61K 8/29* (2013.01); *A61K 8/31* (2013.01); *A61K 8/34* (2013.01); *A61K 8/345* (2013.01); *A61K 8/37* (2013.01); *A61K 8/4973* (2013.01); *A61K 8/585* (2013.01); *A61K 8/732* (2013.01); *A61K 8/8111* (2013.01); *A61K 8/8152* (2013.01); *A61K 8/8158* (2013.01); *A61K 8/85* (2013.01); *A61K 8/87* (2013.01); *A61K 8/89* (2013.01); *A61K 8/891* (2013.01); *A61K 8/895* (2013.01); *A61K 8/92* (2013.01); *A61K 8/922* (2013.01); *A61K 8/97* (2013.01); *A61Q 1/04* (2013.01); *A61Q 1/06* (2013.01); *A61Q 1/10* (2013.01); *A61Q 1/12* (2013.01); *A61Q 19/00* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,266,321 | A | 11/1993 | Shukuzaki et al. |
| 5,470,884 | A | 11/1995 | Corless et al. |
| 6,120,780 | A | 9/2000 | Dupuis et al. |
| 6,187,323 | B1 | 2/2001 | Aiache et al. |
| 6,497,861 | B1 | 12/2002 | Wang et al. |
| 6,916,464 | B2 | 7/2005 | Hansenne et al. |
| 7,942,937 | B2 | 5/2011 | Brun |

(Continued)

FOREIGN PATENT DOCUMENTS

| | | |
|---|---|---|
| EP | 0 388 582 A2 | 9/1990 |
| EP | 0 963 751 A2 | 12/1999 |

(Continued)

OTHER PUBLICATIONS

Seppic, "Sepinov EMT 10", Apr. 2006, pp. 1-19.*
Feb. 23, 2016 Office Action issued in U.S. Appl. No. 14/770,154.
Jul. 15, 2016 Office Action issued in U.S Appl. No. 14/770,154.
Technical data sheet. Viscosity of Carbpool Polymers in Aqueous Systems. Lubrizol. 2009. 10p.
Aug. 1, 2016 Office Action issued in U.S. Appl. No. 14/770,292.
Almeida, et al., "Moisturizing Effect of Oleogel/Hydrogel Mixtures", Pharmaceutical Development and Technology, vol. 13, Jan. 2, 2008, pp. 487-494, XP009174126.
May 9, 2014 Written Opinion of the International Searching Authority issued in PCT Patent Application No. PCT/IB2014/059238.

(Continued)

*Primary Examiner* — Brian Gulledge
(74) *Attorney, Agent, or Firm* — Oliff PLC

(57) ABSTRACT

The present invention is directed towards a cosmetic composition for making up and/or caring for keratin materials, in particular the skin and/or the lips, comprising: —at least one aqueous phase gelled with at least one synthetic polymeric hydrophilic gelling agent; and —at least one oily phase gelled with at least one lipophilic gelling agent chosen from particulate gelling agents, organopolysiloxane elastomers, semi-crystalline polymers and dextrin esters, and mixtures thereof; the said phases forming therein a macroscopically homogeneous mixture.

18 Claims, No Drawings

(56) References Cited

U.S. PATENT DOCUMENTS

| | | | |
|---|---|---|---|
| 8,216,554 | B2 | 7/2012 | Shah et al. |
| 8,333,956 | B2 | 12/2012 | Brieva et al. |
| 8,449,870 | B2 | 5/2013 | Wang et al. |
| 8,858,967 | B2 | 10/2014 | Astruc et al. |
| 2003/0026772 | A1 | 2/2003 | Jager-Lezer et al. |
| 2003/0223943 | A1 | 12/2003 | Uang et al. |
| 2005/0048016 | A1 | 3/2005 | Lebreton et al. |
| 2005/0163730 | A1 | 7/2005 | Rosevear et al. |
| 2005/0196364 | A1 | 9/2005 | Josso |
| 2007/0231354 | A1 | 10/2007 | Sogabe et al. |
| 2008/0064761 | A1 | 3/2008 | Gondek et al. |
| 2010/0221296 | A1 | 9/2010 | Moneuze et al. |
| 2010/0310481 | A1 | 12/2010 | Chevalier et al. |
| 2010/0322983 | A1* | 12/2010 | Griffiths-Brophy ... A61K 8/044 424/401 |
| 2011/0158920 | A1* | 6/2011 | Morley .................. A61K 8/042 424/59 |
| 2017/0189278 | A1 | 7/2017 | Bchir et al. |

FOREIGN PATENT DOCUMENTS

| | | |
|---|---|---|
| EP | 1 818 042 A2 | 8/2007 |
| EP | 2 135 525 A2 | 12/2009 |
| EP | 2 492 333 A1 | 8/2012 |
| FR | 2 986 422 A1 | 8/2013 |
| FR | 2 986 424 A1 | 8/2013 |
| FR | 2 992 203 A1 | 12/2013 |
| JP | S60-6607 A | 1/1985 |
| JP | 2005-112834 A | 4/2005 |
| JP | 2005-232107 A | 9/2005 |
| JP | 2005-314391 A | 11/2005 |
| JP | 2007-217411 A | 8/2007 |
| JP | 2007-527452 A | 9/2007 |
| JP | 2007-262032 A | 10/2007 |
| JP | 2009-502852 A | 1/2009 |
| JP | 2010-006708 A | 1/2010 |
| JP | 2010-111674 A | 5/2010 |
| JP | 2011-088850 A | 5/2011 |
| JP | 2011-213652 A | 10/2011 |
| PT | 2004-05758 A | 9/2006 |
| WO | 99/22696 A1 | 5/1999 |
| WO | 99/62497 A1 | 12/1999 |
| WO | 99/65455 A1 | 12/1999 |
| WO | WO 99/62497 * | 12/1999 |
| WO | WO 99/65455 * | 12/1999 |
| WO | 01/89470 A1 | 11/2001 |
| WO | 2008/081175 A2 | 7/2008 |
| WO | 2008/114732 A1 | 9/2008 |
| WO | 2011-143254 A2 | 11/2011 |
| WO | 2013/087927 A1 | 6/2013 |
| WO | 2013/093869 A2 | 6/2013 |
| WO | 2013/107000 A1 | 7/2013 |
| WO | 2014/128678 A1 | 8/2014 |
| WO | 2014/128680 A1 | 8/2014 |

OTHER PUBLICATIONS

May 9, 2014 International Search Report issued in Patent Application No. PCT/IB2014/059238.
U.S. Appl. No. 14/770,292, filed Aug. 25, 2015 in the name of Valverde et al.
U.S. Appl. No. 14/770,154, filed Aug. 25, 2015 in the name of Veronique et al.
Almeida, et al., "Evaluation of the Physical Stability of Two Oleogels", International Journal of Pharmaceutics, vol. 327, No. 1-2, Dec. 11, 2006, pp. 73-77.
May 15, 2014 Written Opinion of the International Searching Authority issued in PCT Patent Application No. PCT/IB2014/059239.
May 15, 2014 International Search Report issued in Patent Application No. PCT/IB2014/059239.
May 27, 2014 Written Opinion of the International Searching Authority issued in PCT Patent Application No. PCT/IB2014/059240.
May 27, 2014 International Search Report issued in Patent Application No. PCT/IB2014/059240.
Jan. 19, 2017 Office Action Issued in U.S Appl. No. 14/770,292.
Jan. 19, 2018 Office Action issued in U.S. Appl. No. 15/314,221.
Oct. 20, 2017 Third Party Observation issued in Japanese Patent Application No. 2015-558600.
Dow Corning VM-2270 (Aerogel Fine Particles (2012) accessed at http://www.dowcorning.com/content/publishedlit/27-1235.pdf accessed Jan. 10, 2018 (Year: 2012)).
Jan. 9, 2018 Office Action issued in Japanese Application No. 2015-558599.
Jul. 31, 2015 International Search Report issued in International Patent Application No. PCT/IB2015/053953.
Kobayashi. "Oil Up Cosmetic Material Consist Disperse System Silicone Gel Composition Polysiloxane Powder Base Agent". Sep. 14, 1989. XP002735135.
U.S. Appl. No. 15/507,318, filed Feb. 28, 2017 in the name of Roubot et al.
U.S. Appl. No. 15/314,221, filed Nov. 28, 2016 in the name of Bchir et al.
Jan. 13, 2016 International Search Report issued in International Patent Application No. PCT/IB2015/056474.
Jan. 19, 2016 International Search Report issued in International Patent Application No. PCT/IB2015/056471.
Degussa. "Versatile and Effective", Aerosil. Mar. 3, 2003, p. 1-21. XP003026229.
Jan. 13, 2016 Written Opinion issued in International Patent Application No. PCT/IB2015/056474.
Jan. 19, 2016 Written Opinion issued in International Patent Application No. PCT/IB2015/056471.
May 20, 2015 Written Opinion issued in French Patent Application No. 1458034.
Jul. 31, 2015 Written Opinion issued in International Patent Application No. PCT/IB2015/053953.
May 22, 2017 Office Action issued in U.S. Appl. No. 14/770,292.
Jul. 12, 2017 Office Action issued in U.S. Appl. No. 15/314,221.
Jul. 28, 2017 Office Action issued in U.S. Appl. No. 14/770,182.
U.S. Appl. No. 15/507,440, filed Feb. 28, 2017 in the name of Bouarfa et al.
Elizabeth Arden, "Moister Lotion SPF 15," Mintel, pp. 1-3, Record ID: 639186, Jan. 2007.
Marks & Spencer, "Daly Protect Everyday Moisturiser SPF 12," Mintel, pp. 1-3, Record ID: 1448926, Dec. 2010.
Jul. 4, 2017 Third Party Observation issued in European Application No. 14710991.2.
Jul. 13, 2017 Third Party Observation issued in European Application No. 14708695.3.
Scrubs, "Instant Lifting Cream," Mintel, Record ID: 1912786, pp. 1-3, Nov. 2012.
Jul. 2, 2018 Office Action issued in U.S. Appl. No. 15/507,440.
Apr. 5, 2018 Office Action issued in U.S. Appl. No. 15/507,440.
Apr. 19, 2018 Office Action issued in U.S. Appl. No. 14/770,154.
May 4, 2018 Office Action issue in U.S. Appl. No. 14/770,292.
May 23, 2018 Office Action issued in U.S. Appl. No. 15/507,318.
Oct. 4, 2018 Office Action issued in U.S. Appl. No. 15/314,221.
Nov. 30, 2018 Office Action issued in U.S. Appl. No. 14/770,292.
Elementis Specialties, "Bentonite Gel ISD V," pp. 1-11, 2008.
Dec. 10, 2018 Office Action issued in U.S. Appl. No. 14/770,154.
Dec. 20, 2018 Office Action issued in U.S. Appl. No. 15/507,318.
Annamarya Scaccia, "What Are the Benefits of Using Avocado Oil on My Skin?," Health Line News Letter, Downloaded from https://www.healthline.com/health /beauty-skin-care/ avocado-oil-for-skin on Dec. 14, 2018, (Year 2018).
Unknown Author, "Safety Assessment of Alkoxy Polysiloxane as Used in Cosmetics," released Feb. 21, 2014 (only pertinent portion is provided), (Year 2014).

* cited by examiner

GEL-TYPE COSMETIC COMPOSITION

The present invention is directed towards proposing for the field of caring for and making up keratin materials, especially the skin and/or the lips, and in particular the skin, a novel galenical form that is most particularly advantageous with regard to its technical performance and the sensations it affords the user during its application, in particular to the skin.

The term "keratin materials" especially means the skin, the lips and/or the eyelashes, in particular the skin and/or the lips, and preferably the skin.

Conventionally, a cosmetic composition formulator uses emulsified systems combining an aqueous phase for freshness and an oily phase for comfort. The strong point of these systems is also that they allow the combination, within the same composition, of cosmetic active agents that have different affinities with respect to these two aqueous and oily phases.

Unfortunately, these emulsifying systems do not lend themselves to rapid and easy production of an infinite range of compositions. Thus, for a given emulsifying system, it often proves complicated to functionalize the formulation by adding, for example, an antisun product, certain active agents, pigments, polymers, fragrances or fillers, etc. without impairing the stability, the sensory properties and the quality of the film deposited on the keratin materials and especially the skin. The formulation then needs to be readjusted. It is also difficult to reconcile, within the same composition, opposing technical performance qualities, for instance mattness (which may make the skin dry) and moisturization (which may make the skin shiny).

Furthermore, emulsified systems do not lend themselves to the formulation of all the ingredients or active agents liable to be considered in the field of care or makeup, or even to the formulation of high contents of certain cosmetic ingredients or active agents. Non-compliance with these incompatibilities has the consequence of destabilizing the emulsified architecture, which then, inter alia, undergoes demixing.

Finally, these emulsified systems do not lend themselves to rapid and easy production of an infinite range of textures.

Moreover, in the case of making up the complexion, the preferred emulsifying systems are mainly reverse emulsions with regard to the good level of coverage and the homogeneous appearance they afford when compared with direct emulsions. On the other hand, their weak point is a high greasy and tacky sensation, and thus a lack of lightness as regards the textures obtained.

Galenical formulations of gel/gel type partially meet these expectations (Almeida et al., Pharmaceutical Development and Technology, 2008, 13:487, tables 1 and 2, page 488; WO 99/65455; PI 0405758-9; WO 99/62497; JP 2005-112834 and WO 2008/081 175). Formulations of this type combine a gelled aqueous phase with a gelled oily phase. In fact, these gel/gel formulations were essentially proposed as an advantageous alternative to emulsifying systems on the grounds that they make it possible to dispense with the use of the surfactants required for the stability and texturization of emulsions. Unfortunately, besides this advantage, the gel/gel formulations described hitherto do not essentially reveal any novel or improved technical performance qualities.

It therefore remains difficult for a person skilled in the art to propose homogeneous compositions that are capable of affording an immediate visual result on the skin with a light sensation on application, this expected immediate result preferentially being good coverage of colour imperfections and/or of relief imperfections, without, however, marking them. It is therefore necessary to find novel systems for distributing on the skin components such as water, fatty substances and solid particles.

These novel architectures must be entirely satisfactory to users as regards the sensation afforded, but must also be capable of affording improved cosmetic properties, or must even have an increased number of technical performance qualities such as freshness, lightness, emollience, comfort, coverage of imperfections, colour, unifying aspect, lightening, etc., and, on the other hand, must be free of the known side effects of oily and aqueous phases such as, respectively, a greasy feel, a tacky feel, a feeling of lack of glidance or alternatively a feeling of dragging on application.

The inventors have now found, unexpectedly, that such an objective can be achieved via the choice of a system of specific hydrophilic gelling agent(s)/lipophilic gelling agent(s) for the preparation of a cosmetic composition of the type such as a bi-continuous but on the other hand macroscopically homogeneous system which has a large number of technical performance qualities and which furthermore has optimized effects.

More precisely, the inventors have found that the choice of a system of specific hydrophilic gelling agent(s)/lipophilic gelling agent(s) makes it possible, contrary to all expectation, to combine in a single composition a significant number of technical performance qualities, with the intensity of each performance quality advantageously not being attenuated by the manifestation of other associated performance qualities, or even being, for certain performance qualities, stimulated.

Thus, according to one of its aspects, the present invention relates to a cosmetic composition for making up and/or caring for keratin materials, in particular the skin and/or the lips, comprising:
  at least one aqueous phase gelled with at least one synthetic polymeric hydrophilic gelling agent; and
  at least one oily phase gelled with at least one lipophilic gelling agent chosen from particulate gelling agents, organopolysiloxane elastomers, semi-crystalline polymers and dextrin esters, and mixtures thereof;
the said phases forming therein a macroscopically homogeneous mixture.

According to one embodiment variant, a composition according to the invention consists of an aqueous phase gelled with at least one synthetic polymeric hydrophilic gelling agent, and an oily phase gelled with at least one lipophilic gelling agent chosen from particulate gelling agents, organopolysiloxane elastomers, semi-crystalline polymers and dextrin esters, and mixtures thereof.

According to a preferred variant, a composition according to the invention also contains at least one dyestuff.

This dyestuff may be chosen from pigments, and water-soluble or liposoluble dyestuffs, especially as detailed below.

In particular, the dyestuffs are pigments.

According to an advantageous embodiment variant, the dyestuff is conveyed at least in the gelled oily phase.

As stated above, the inventors have found, contrary to all expectation, that the choice of particular hydrophilic gelling agent(s)/lipophilic gelling agent(s) couples for texturing a composition of gel/gel type makes it possible to significantly improve certain technical performance qualities, and to dispense with certain adverse effects inherent in the gelling agents under consideration, or even to reconcile within this composition properties which it was hitherto difficult to make coexist. Furthermore, as emerges from the examples below, the present invention moreover makes it possible, unexpectedly, to optimize some of the expected technical performance qualities.

For example, an aqueous phase textured according to the invention with an oily gelling agent of organopolysiloxane elastomer type, which is advantageous for its mattifying properties, makes it possible, when it is combined with an aqueous phase gelled with an acrylic polymer, to gain access to a cosmetic composition that is most particularly advantageous for caring for and making up greasy and combination skin since it has mattifying properties and a freshness effect, and for which the dragging effect, which is a known side effect of aqueous gelling agents, is unexpectedly found to be significantly attenuated.

Similarly, an oily phase gelled with a wax makes it possible, when it is combined with an aqueous phase gelled with an acrylic polymer, to gain access to a cosmetic composition that is most particularly advantageous for caring for and making up normal skin, since it has emollient properties and a freshness effect, but for which the greasy feel, which is a known side effect of waxes, is found to be significantly attenuated.

The inventors have also found, surprisingly, that the soft-focus performance quality of a composition according to the invention comprising aqueous and oily phases gelled, respectively, with a polymeric or particulate gelling agent with a soft-focus effect proves to be significantly improved. The gain in soft-focus effect proves to be greater than the sum of the respective optical effects of each of the two gelled phases in each of the two compositions. There is manifestly synergism.

In addition, the inventors have surprisingly found that compositions according to the invention allow obtaining pigmented "self-smoothing" formulations which are homogeneous and stable without requiring the presence of a surfactant, in particular when a nonionic associative polymer of polyurethane type is used as gelling agent of the aqueous phase. Moreover, such compositions have a homogeneous deposit upon application. In particular, the use of nonionic associative polymer of polyurethane type, such as nonionic fatty-chain polyurethane polyethers, allows to form composition having a dense and elastic texture, which enables to dose the grip of the composition.

In addition, by virtue of the associative polyurethane, the so-obtained compositions have the advantage of being "self-smoothing", whose surface regains its smoothness after use. After each use, a smooth and uniform surface reforms at the surface of the jar, as if the jar was new, and when the cream is taken up on a finger or any other means (sponge or spatula), the mark of this finger or of this means does not remain at all.

The compositions according to the invention also prove to be very stable and not subject to syneresis.

Besides the abovementioned unexpected advantages, the gelling system under consideration according to the invention affords a texture that is sufficiently thickened to be compatible with the formulation of a very wide diversity of ingredients or active agents. It combines in a single formulation a large number of functional active agents or ingredients (fillers, pigments, etc.).

In particular, the compositions according to the invention also prove to be very advantageous for formulating high amount of particulate materials, like pigments and fillers, as requested in conventional compositions dedicated to make-up.

It is known that compositions having high amounts of aqueous phase, like more than 30% by weight, are not always convenient for formulating solid materials in amount of more than 10%. However, such high amounts of particles are generally necessary to get the expected properties of make-up as coverage and/or masking of skin imperfections.

The compositions according to the invention allow precisely formulating high amounts of solid materials while keeping the expected properties of a make-up composition, namely lightness, freshness and comfort. Moreover, the compositions according to the invention maintain the make-up properties, as good coverage, colored effect and relief masking.

At last, the composition is easy to apply on the surface of the targeted keratin material. This performance is notably technically characterized by a good playtime.

According to another of its aspects, a subject of the invention is also a process for preparing a cosmetic composition for making up and/or caring for keratin materials, in particular the skin and/or the lips, comprising at least one step of mixing:
  at least one aqueous phase gelled with at least one synthetic polymeric hydrophilic gelling agent; and
  at least one oily phase gelled with at least one lipophilic gelling agent chosen from particulate gelling agents, organopolysiloxane elastomers, semi-crystalline polymers and dextrin esters, and mixtures thereof;
under conditions suitable for obtaining a macroscopically homogeneous mixture.

According to one embodiment variant, this process may advantageously comprise a step of mixing at least three or even more gelled phases.

For obvious reasons, the number of gelled aqueous phases and of gelled oily phases to be considered for forming a composition according to the invention may range for each of the two types of phase beyond two. It is especially conditioned by the number of expected technical performance qualities.

For example, this process may use a single gelled aqueous phase and two oily phases gelled with different lipophilic gelling agents.

Conversely, this process may also use a single gelled oily phase and two aqueous phases gelled with different hydrophilic gelling agents.

For example, the phases having the same architecture, namely aqueous or oily, may be precombined to form a premix, and it is this premix which is placed in contact with the phase or even with a premix of several phases having the other architecture. The corresponding aqueous and oily gels may be prepared separately without heating, without requiring the necessary presence of surfactants in order to achieve the desired architecture. Thus, in addition to the advantages mentioned above, the claimed compositions may be readily prepared at reduced cost.

Advantageously, the mixing of the phases may be performed at room temperature.

However, the process of the invention may comprise, if necessary, a step of heating the mixture.

The process according to the invention thus offers the formulator a simple and rapid means for gaining access to a multitude of cosmetic compositions having common performance qualities but also performance qualities that are specific to each of its compositions.

The present invention also gives the user access to this faculty of mixing at least two phases of the same architecture with at least one phase of different architecture via the provision of a cosmetic kit for making up and/or caring for keratin materials.

Thus, according to another of its aspects, the present invention relates to a cosmetic kit for making up and/or caring for keratin materials, in particular the skin and/or the lips, comprising, in separate containers, at least one aqueous phase gelled with at least one synthetic polymeric hydrophilic gelling agent; and at least one oily phase gelled with at least one lipophilic gelling agent chosen from particulate gelling agents, organopolysiloxane elastomers, semi-crystalline polymers and dextrin esters, and mixtures thereof, and also to instructions for using the extemporaneous mixtures.

According to yet another of its aspects, the present invention relates to a device for making up and/or caring for keratin materials, in particular the skin and/or the lips, comprising at least:
  two separate containers containing, respectively, at least one aqueous phase gelled with at least one synthetic polymeric hydrophilic gelling agent; and at least one oily phase gelled with at least one lipophilic gelling agent chosen from particulate gelling agents, organopolysiloxane elastomers, semi-crystalline polymers and dextrin esters, and mixtures thereof;
  a distinct chamber for mixing the said containers, comprising an aperture configured to allow the introduction of the said phases to be mixed; and
  a means for distributing a macroscopically homogeneous mixture of the two phases.

According to an advantageous variant, the kits and devices according to the invention contain at least two, or even more, different gelled phases for each of the two types of aqueous and oily architecture.

According to a particular embodiment, the representative gelled phases of the same type of architecture are gelled with a different gelling agent.

Multi-phase formulations of "patchwork" type may thus be developed.

According to another particular embodiment, the representative gelled phases of the same type of architecture are different as regards their optical properties. For example, the kit or device may propose two oily gels phases textured by the same oily gelling agent, but one containing dyestuffs and the other not. The user thus has the possibility of exploiting or not exploiting makeup performance quality in addition to the other performance qualities.

A kit or device according to the invention also allows the user to modify the intensity of the colour effect by adjusting the proportion of the coloured gelled phase to be mixed.

Thus, the kits and devices according to the invention are particularly advantageous in so far as they afford the user the possibility of adjusting at will, by means of the choice of the gelled phases representative of the two types of oily and aqueous architecture, the desired makeup performance qualities, while at the same time ensuring convenience and ease of use.

The present invention especially makes it possible to afford the user a wider makeup range and also to give the makeup operation an appealing fun aspect. Moreover, the fact that the mixing of the phases may be performed at room temperature is of manifest interest as regards the convenience and thus gives satisfaction as regards the simplicity of use.

According to another of its aspects, a subject of the invention is also a process, especially a cosmetic process, for making up and/or caring for a keratin material, in particular the skin and/or the lips, comprising at least one step that consists in applying to the said keratin material a composition in accordance with the invention.

According to yet another of its aspects, the present invention relates to a process, especially a cosmetic process, for caring for and/or making up a keratin material, in particular the skin and/or the lips, comprising at least the application to the said material of a composition, in particular a macroscopically homogeneous composition obtained by extemporaneous mixing, before application or at the time of application to the said keratin material, of at least one aqueous phase gelled with at least one synthetic polymeric hydrophilic gelling agent, and of at least one oily phase gelled with at least one lipophilic gelling agent chosen from particulate gelling agents, organopolysiloxane elastomers, semi-crystalline polymers and dextrin esters, and mixtures thereof.

Cosmetic Composition

Firstly, it is important to note that a composition according to the invention is different from an emulsion.

An emulsion generally consists of an oily liquid phase and an aqueous liquid phase. It is a dispersion of droplets of one of the two liquid phases in the other. The size of the droplets forming the dispersed phase of the emulsion is typically about a micrometer (0.1 to 100 µm). Furthermore, an emulsion requires the presence of a surfactant or of a silicone emulsifier to ensure its stability over time.

In contrast, a composition according to the invention consists of a macroscopically homogeneous mixture of two immiscible gelled phases. These two phases both have a gel-type texture. This texture is especially reflected visually by a consistent, creamy appearance.

The terms "macroscopically homogeneous mixture" means a mixture in which each of the gelled phases cannot be individualized with the naked eye.

More precisely, in a composition according to the invention, the gelled aqueous phase and the gelled oily phase interpenetrate and thus form a stable and, consistent product. This consistency is achieved by mixing interpenetrated oily and aqueous gelled macrodomains. These interpenetrated macrodomains are not measurable objects. Thus, by microscope, the composition according to the invention is very different from an emulsion. It cannot be characterized either as having a "sense", i.e. an O/W or W/O sense.

Thus, a composition according to the invention has a consistency of gel type. Furthermore, the stability of the composition is long-lasting without surfactant. Consequently, a cosmetic composition according to the invention does not require any surfactant or silicone emulsifier to ensure its stability over time.

It is known from the state of the art to observe the intimate nature of the mixture of the aqueous and oily gels in a gel-type composition, for example, by introducing a dye substance into either the oily or aqueous gel phases before forming the gel-type composition. On visual inspection, the dye is seen to be uniformly dispersed, even though the dye is present in only one of the oily gel or aqueous gel. Indeed, if two different dyes of different colours are introduced into the oily and aqueous phases, respectively, before forming the gel-type composition, both colours can be observed uniformly dispersed throughout the gel-type composition. This is in contrast to an emulsion wherein if a dye that is either water-soluble or oil-soluble is introduced into the aqueous or oily phases, respectively, before forming an emulsion, only the colour of the dye in the external phase will be observed (Remington: The Science and Practice of Pharmacy, 19th Edition (1995) Chapter 21, page 282).

It is also known to distinguish a gel-type composition from an emulsion by performing a "drop test". This test consists to demonstrate the bi-continous nature of a gel-type composition. Indeed, as mentioned above, the composition's consistency is achieved by interpenetrating oily and aqueous gelled domains. Therefore, the bi-continous nature of a gel-type composition can be highlighted by a simple test with respectively hydrophilic and hydrophobic solvents. This test consists to deposit, on the one hand, a droplet of a hydrophilic solvent on a first sample of the tested composition, and, on the other hand, a droplet of a hydrophobic solvent on a second sample of the same tested composition, and to analyze the behavior of both droplets of solvents. In the case of an O/W emulsion, a droplet of hydrophilic solvent diffuses in the sample and a droplet of hydrophobic solvent remains at the sample surface. In the case of a W/O emulsion, a droplet of hydrophilic solvent remains at the sample surface and a droplet of hydrophobic solvent diffuses throughout sample. Finally, in the case of a gel-type composition (bi-continuous system), the hydrophilic and hydrophobic droplets diffuse in the entire sample.

In particular, in the case of the present invention, the test which will be privileged for distinguishing a gel-type composition from an emulsion consists in a dilution test. Indeed, in a gel-type composition, the gelled aqueous domains and gel oily domains interpenetrate and form a stable and consistent product, whose dilution behavior in water and oil is different of emulsion's behavior. Therefore, the dilution behavior of a gel-type composition (bi-continuous system) can be compared to emulsions.

More specifically, the dilution test consists to put 40 g of product plus 160 g of dilution solvent (water or oil) in a 30 ml plastic beaker. The dilution is performed under controlled agitation to avoid any phenomenon of emulsification. In particular, it is done using a planetary mixer: Speed Mixer TM DAC400FVZ. The Speed Mixer is set to 1500 rpm for 4 minutes. Finally, observation of resulting sample is made with a light microscope at a magnification of ×100 (×10× 10). It may be noticed that oils like Parleam® and Xiameter PMX-200 Silicone Fluid 5CS® from Dow Corning are convenient as dilution solvents.

In the case of a gel-type composition (bi-continuous system), when diluted either in oil or water, a heterogeneous aspect is always observed. When a gel-type composition (bi-continuous system) is diluted with water, one will observe lumps of oily gel in suspension and when a gel-type composition (bi-continuous system) is diluted with oil, one will observe lumps of aqueous gel in suspension.

On the contrary, upon dilution, emulsions display a different behavior. An O/W emulsion when it is diluted with an aqueous solvent will gradually thin up without presenting a heterogeneous and lumpy aspect. This same O/W emulsion when diluted with oil will present a heterogeneous appearance (lumps of O/W emulsion suspended in oil). A W/O emulsion when diluted with an aqueous solvent will present a heterogeneous appearance (lumps of W/O emulsion is suspended in the water). This same W/O emulsion when diluted with oil will gradually thin up without presenting a heterogeneous and lumpy aspect.

In general, the aqueous gelled phase and the oily gelled phase forming a composition according to the invention are present in a weight ratio ranging from 95/5 to 5/95. More preferentially, the aqueous phase and the oily phase are present in a weight ratio ranging from 30/70 to 80/20.

The ratio between the two gelled phases is adjusted according to the desired cosmetic properties.

Thus, in the case of a composition intended for making up the skin and especially the face, it is advantageous to favour an aqueous phase/oily phase weight ratio greater than 1, especially ranging from 60/40 to 90/10, preferably ranging from 60/40 to 80/20, preferably from 60/40 to 70/30 and more preferably to favour an aqueous phase/oily phase weight ratio of 60/40 or 70/30.

These preferred ratios are particularly advantageous for obtaining fresh and light compositions.

Advantageously, a composition according to the invention is in the form of a creamy gel with a minimum stress below which it does not flow unless it has been subjected to an external mechanical stress.

As emerges from the text hereinbelow, a composition according to the invention may have a minimum threshold stress of 1.5 Pa and in particular greater than 10 Pa.

It also advantageously has a stiffness modulus G* at least equal to 400 Pa and preferably greater than 1000 Pa.

According to an advantageous embodiment variant, the gelled phases under consideration to form a composition according to the invention have, respectively, a threshold stress of greater than 1.5 Pa and preferably greater than 10 Pa.

Characterization of the threshold stresses is performed by oscillating rheology measurements. A method is proposed in the examples section of the present text.

In general, the corresponding measurements are taken at 25° C. using a Haake RS600 imposed-stress rheometer equipped with a plate-plate measuring body (60 mm diameter) fitted with an anti-evaporation device (bell jar). For each measurement, the sample is placed delicately in position and the measurements start 5 minutes after placing the sample in the air gap (2 mm). The composition is then subjected to a stress ramp from $10^{-2}$ to $10^3$ Pa at a set frequency of 1 Hz.

A composition according to the invention may also have a certain elasticity. This elasticity may be characterized by a stiffness modulus G* which, under this minimum stress threshold, may be at least equal to 400 Pa and preferably greater than 1000 Pa. The value G* of a composition may be obtained by subjecting the composition under consideration to a stress ramp from $10^{-2}$ to $10^3$ Pa at a set frequency of 1 Hz.

Hydrophilic Gelling Agent

For the purposes of the present invention, the term "hydrophilic gelling agent" means a compound that is capable of gelling the aqueous phase of the compositions according to the invention.

The gelling agent is hydrophilic and is thus present in the aqueous phase of the composition.

The gelling agent may be water-soluble or water-dispersible.

As stated above, the aqueous phase of a composition according to the invention is gelled with at least one hydrophilic gelling agent chosen from synthetic polymeric gelling agents.

For the purposes of the invention, the term "synthetic" means that the polymer is neither naturally existing nor a derivative of a polymer of natural origin.

The synthetic polymeric hydrophilic gelling agent under consideration according to the invention may or may not be particulate.

For the purposes of the invention, the term "particulate" means that the polymer is in the form of particles, preferably spherical particles.

Advantageously, a composition according to the invention comprises a polymeric hydrophilic gelling agent chosen from crosslinked acrylic homopolymers or copolymers; associative polymers, in particular associative polymers of polyurethane type; polyacrylamides and crosslinked and/or neutralized 2-acrylamido-2-methylpropanesulfonic acid polymers and copolymers; modified or unmodified carboxyvinyl polymers, and mixtures thereof, especially as defined below.

A. Particulate Synthetic Polymeric Gelling Agents

They are preferably chosen from crosslinked polymers.

They may especially be crosslinked acrylic homopolymers or copolymers, which are preferably partially neutralized or neutralized, and which are in particulate form.

According to one embodiment, the particulate gelling agent according to the present invention is chosen from crosslinked sodium polyacrylates. Preferably, it has in the dry or non-hydrated state a mean size of less than or equal to 100 µm and preferably less than or equal to 50 µm. The mean size of the particles corresponds to the mass-average diameter (D50) measured by laser particle size analysis or another equivalent method known to those skilled in the art.

Thus, preferably, the particulate gelling agent according to the present invention is chosen from crosslinked sodium polyacrylates, preferably in the form of particles with a mean size (or mean diameter) of less than or equal to 100 microns, more preferably in the form of spherical particles.

As examples of crosslinked sodium polyacrylates, mention may be made of those sold under the brand names Octacare X100, X110 and RM100 by the company Avecia, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/Sodium acrylate copolymer) by the company Grain Processing.

Mention may also be made of crosslinked polyacrylate microspheres, for instance those sold under the name Aquakeep® 10 SH NF by the company Sumitomo Seika.

Such gelling agents may be used in a proportion of from 0.1% to 5% by weight of solids relative to the total weight of the aqueous phase, especially from 0.5% to 2% by weight and in particular in a proportion of about from 0.8% to 1.7% by weight, relative to the total weight of the aqueous phase.

B. Non-Particulate Synthetic Polymeric Gelling Agents

This family of gelling agents may be detailed under the following subfamilies:
 1. Associative polymers,
 2. Crosslinked and/or neutralized 2-acrylamido-2-methylpropanesulfonic acid polymers and copolymers, and
 3. Modified or unmodified carboxyvinyl polymers.

B.1 Associative Polymers

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, advantageously by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2OB_nR \quad (I)$$

in which R' denotes H or $CH_3$, B denotes the ethylenoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms.

Anionic amphiphilic polymers of this type are described and prepared, according to an emulsion polymerization process, in patent EP 0 216 479.

Among the associative anionic polymers that may also be mentioned are maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

Among the associative anionic polymers, it is possible, according to a preferred embodiment, to use copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 OE units) terpolymer or Aculyn 28 (methacrylic acid/ethyl acrylate/oxyethylenated behenyl methacrylate (25 OE) terpolymer).

Examples of associative anionic polymers that may also be mentioned include anionic polymers comprising at least one hydrophilic unit of unsaturated olefinic carboxylic acid type, and at least one hydrophobic unit exclusively of the type such as a ($C_{10}$-$C_{30}$) alkyl ester of an unsaturated carboxylic acid. Examples that may be mentioned include the anionic polymers described and prepared according to patents US Pat. Nos. 3,915,921 and 4,509,949.

Associative anionic polymers that may also be mentioned include anionic terpolymers The anionic terpolymer used according to the invention is a linear or branched and/or crosslinked terpolymer, of at least one monomer (1) bearing an acid function in free form, which is partially or totally salified with a nonionic monomer (2) chosen from N,N-dimethylacrylamide and 2-hydroxyethyl acrylate and at least one polyoxyethylenated alkyl acrylate monomer (3) of formula (I) below:

$$（I）$$

[chemical structure]

in which R1 represents a hydrogen atom, R represents a linear or branched $C_2$-$C_8$ alkyl radical and n represents a number ranging from 1 to 10.

The term "branched polymer" denotes a non-linear polymer which bears side chains so as to obtain, when this polymer is dissolved in water, a high degree of entanglement leading to very high viscosities, at a low speed gradient.

The term "crosslinked polymer" denotes a non-linear polymer which is in the form of a three-dimensional network that is insoluble in water but swellable in water, leading to the production of a chemical gel.

The acid function of the monomer (1) is especially a sulfonic acid or phosphonic acid function, the said functions being in free or partially or totally salified form.

The monomer (1) may be chosen from styrenesulfonic acid, ethylsulfonic acid and 2-methyl-2-[(1-oxo-2-propenyl) amino]-1-propanesulfonic acid (also known as acryloyldimethyl taurate), in free or partially or totally salified form. It is present in the anionic terpolymer preferably in molar proportions of between 5 mol % and 95 mol % and more particularly between 10 mol % and 90 mol %. The monomer (1) will more particularly be 2-methyl-2-[(1-oxo-2-propenyl)amino]-1-propanesulfonic acid in free or partially or totally salified form.

The acid function in partially or totally salified form will preferably be an alkali metal salt such as a sodium or potassium salt, an ammonium salt, an amino alcohol salt such as a monoethanolamine salt, or an amino acid salt such as a lysine salt.

The monomer (2) is preferably present in the anionic terpolymer in molar proportions of between 4.9 mol % and 90 mol %, more particularly between 9.5 mol % and 85 mol % and even more particularly between 19.5 mol % and 75 mol %.

In formula (I), examples of linear $C_8$-$C_{16}$ alkyl radicals that may be mentioned include octyl, decyl, undecyl, tridecyl, tetradecyl, pentadecyl and hexadecyl.

In formula (I), examples of branched $C_8$-$C_{16}$ alkyl radicals that may be mentioned include 2-ethylhexyl, 2-propylheptyl, 2-butyloctyl, 2-pentylnonyl, 2-hexyldecyl, 4-methylpentyl, 5-methylhexyl, 6-methylheptyl, 15-methylpentadecyl, 16-methylheptadecyl and 2-hexyloctyl.

According to a particular form of the invention, in formula (I), R denotes a $C_{12}$-$C_{16}$ alkyl radical.

According to a particular form of the invention, in formula (I), n ranges from 3 to 5.

Tetraethoxylated lauryl acrylate will more particularly be used as monomer of formula (I).

The monomer (3) of formula (I) is preferably present in the anionic terpolymer in molar proportions of between 0.1 mol % and 10 mol % and more particularly between 0.5 mol % and 5 mol %.

According to a particular mode of the invention, the anionic terpolymer is crosslinked and/or branched with a diethylenic or polyethylenic compound in the proportion expressed relative to the total amount of monomers used, from 0.005 mol % to 1 mol %, preferably from 0.01 mol % to 0.5 mol % and more particularly from 0.01 mol % to 0.25 mol %.

The crosslinking agent and/or branching agent is preferably chosen from ethylene glycol dimethacrylate, diallyloxyacetic acid or a salt thereof, such as sodium diallyloxyacetate, tetraallyloxyethane, ethylene glycol diacrylate, diallylurea, triallylamine, trimethylolpropane triacrylate and methylenebis(acrylamide), or mixtures thereof.

The anionic terpolymer may contain additives such as complexing agents, transfer agents or chain-limiting agents.

Use will be made more particularly of an anionic terpolymer of 2-methyl-2-[(1-oxo-2-propenyl)amino]-1-propanesulfonic acid partially or totally salified form of the ammonium salt, N,N-dimethylacrylamide and tetraethoxylated lauryl acrylate crosslinked with trimethylolpropane triacrylate, of INCI name Polyacrylate Crosspolymer-6, such as the product sold under the trade name Sepimax Zen® by the company SEPPIC.

Cationic Associative Polymers

Cationic associative polymers that may be mentioned include polyacrylates bearing amine side groups.

The polyacrylates bearing quaternized or non-quaternized amine side groups contain, for example, hydrophobic groups of the type such as steareth-20 (polyoxyethylenated (20) stearyl alcohol).

Examples of polyacrylates bearing amino side chains that may be mentioned are the polymers 8781-121B or 9492-103 from the company National Starch.

Nonionic Associative Polymers

The nonionic associative polymers may be chosen from:
copolymers of vinylpyrrolidone and of fatty-chain hydrophobic monomers;
copolymers of $C_1$-$C_6$ alkyl methacrylates or acrylates and of amphiphilic monomers comprising at least one fatty chain;
copolymers of hydrophilic methacrylates or acrylates and of hydrophobic monomers comprising at least one fatty chain, for instance the polyethylene glycol methacrylate/lauryl methacrylate copolymer;
associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisioned. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to a preferred embodiment, a nonionic associative polymer of polyurethane type is used as gelling agent.

As examples of nonionic fatty-chain polyurethane polyethers that may be used in the invention, it is also possible to use Rheolate® FX 1100 (Steareth-100/PEG 136/HDI (hexamethyl diisocyanate) copolymer), Rheolate® 205® containing a urea function, sold by the company Elementis, or Rheolate® 208, 204 or 212, and also Acrysol® RM 184 or Acrysol® RM 2020.

Mention may also be made of the product Elfacos® T210 containing a $C_{12}$-$C_{14}$ alkyl chain, and the product Elfacos® T212 containing a $C_{16-18}$ alkyl chain (PPG-14 Palmeth-60 Hexyl Dicarbamate), from Akzo.

The product DW 1206B® from Röhm & Haas containing a $C_{20}$ alkyl chain and a urethane bond, sold at a solids content of 20% in water, may also be used.

It is also possible to use solutions or dispersions of these polymers, in particular in water or in aqueous-alcoholic medium. Examples of such polymers that may be mentioned are Rheolate® 255, Rheolate® 278 and Rheolate® 244 sold by the company Elementis. Use may also be made of the products DW 1206F and DW 1206J sold by the company Röhm & Haas.

The associative polyurethanes that may be used according to the invention are in particular those described in the article by G. Fonnum, J. Bakke and Fk. Hansen-Colloid Polym. Sci., 271, 380-389 (1993).

Even more particularly, according to the invention, use may also be made of an associative polyurethane that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn® 46 and Aculyn® 44; Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%), and Aculyn® 44 is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%).

Use may also be made of solutions or dispersions of these polymers, especially in water or in aqueous-alcoholic medium. Examples of such polymers that may be mentioned include SER AD FX1010, SER AD FX1035 and SER AD 1070 from the company Elementis, and Rheolate® 255, Rheolate® 278 and Rheolate® 244 sold by the company Elementis. Use may also be made of the products Aculyn® 44, Aculyn® 46, DW 1206F and DW 1206J, and also Acrysol® RVI 184 from the company Röhm & Haas, or alternatively Borchi Gel LW 44 from the company Borchers, and mixtures thereof.

Amphoteric Associative Polymers

Among the associative amphoteric polymers of the invention, mention may be made of crosslinked or non-crosslinked, branched or unbranched amphoteric polymers, which may be obtained by copolymerization:

1) of at least one monomer of formula (IVa) or (IVb):

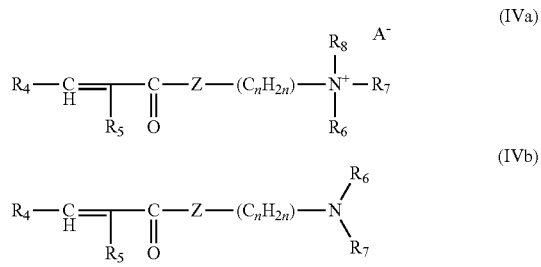

in which R4 and R5, which may be identical or different, represent a hydrogen atom or a methyl radical;

$R_6$, $R_7$ and $R_8$, which may be identical or different, represent a linear or branched alkyl radical containing from 1 to 30 carbon atoms;

Z represents an NH group or an oxygen atom;

n is an integer from 2 to 5;

$A^-$ is an anion derived from an organic or mineral acid, such as a methosulfate anion or a halide such as chloride or bromide;

2) of at least one monomer of formula (V):

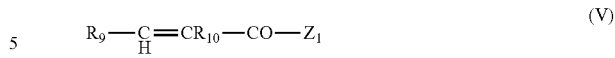

in which R9 and R10, which may be identical or different, represent a hydrogen atom or a methyl radical;

$Z_1$ represents a group OH or a group NHC$(CH_3)_2CH_2SO_3H$;

3) of at least one monomer of formula (VI):

in which R9 and R10, which may be identical or different, represent a hydrogen atom or a methyl radical, X denotes an oxygen or nitrogen atom and R11 denotes a linear or branched alkyl radical containing from 1 to 30 carbon atoms;

4) optionally at least one crosslinking or branching agent; at least one of the monomers of formula (IVa), (IVb) or (VI) comprising at least one fatty chain containing from 8 to 30 carbon atoms and said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group formed by:
  dimethylaminoethyl methacrylate, dimethylaminoethyl acrylate,
  diethylaminoethyl methacrylate, diethylaminoethyl acrylate,
  dimethylaminopropyl methacrylate, dimethylaminopropyl acrylate,
  dimethylaminopropylmethacrylamide or dimethylaminopropylacrylamide, optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyl-trimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers have a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

According to a preferred embodiment, the associative polymer is chosen from nonionic associative polymers and more particularly from associative polyurethanes, such as Steareth-100/PEG-136/HDI Copolymer sold under the name Rheolate FX 1100 by Elementis.

Such an associative polymer is advantageously used in a proportion of from 0.1% to 8% by weight of solids and preferably about 3% by weight, relative to the total weight of the aqueous phase.

B.2 Polyacrylamides and Crosslinked and/or Neutralized 2-Acrylamido-2-Methylpropanesulfonic Acid Polymers and Copolymers The polymers used that are suitable as aqueous gelling agent for the invention may be crosslinked or non-crosslinked homopolymers or copolymers comprising at least the 2-acrylamidomethylpropanesulfonic acid (AMPS®) monomer, in a form partially or totally neutralized with a mineral base other than aqueous ammonia, such as sodium hydroxide or potassium hydroxide.

They are preferably totally or almost totally neutralized, i.e. at least 90% neutralized.

These AMPS® polymers according to the invention may be crosslinked or non-crosslinked.

When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS® polymers that are suitable for use in the invention are water-soluble or water-dispersible. They are in this case:
- either "homopolymers" comprising only AMPS monomers and, if they are crosslinked, one or more crosslinking agents such as those defined above;
- or copolymers obtained from AMPS® and from one or more hydrophilic or hydrophobic ethylenically unsaturated monomers and, if they are crosslinked, one or more crosslinking agents such as those defined above. When said copolymers comprise hydrophobic ethylenically unsaturated monomers, the latter do not comprise a fatty chain and are preferably present in small amounts.

For the purpose of the present invention, the term "fatty chain" is intended to mean any hydrocarbon-based chain containing at least 7 carbon atoms.

The term "water-soluble or water-dispersible" means polymers which, when introduced into an aqueous phase at 25° C., at a mass concentration equal to 1%, make it possible to obtain a macroscopically homogeneous and transparent solution, i.e. a solution with a maximum light transmittance value, at a wavelength equal to 500 nm, through a sample 1 cm thick, of at least 60% and preferably of at least 70%.

The "homopolymers" according to the invention are preferably crosslinked and neutralized, and they may be obtained according to the preparation process comprising the following steps:

(a) the monomer such as AMPS in free form is dispersed or dissolved in a solution of tert-butanol or of water and tert-butanol;

(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;

(c) the crosslinking monomer(s) are added to the solution or dispersion obtained in (b);

(d) a standard free-radical polymerization is performed in the presence of free-radical initiators at a temperature ranging from 10 to 150° C.; the polymer precipitates in the tert-butanol-based solution or dispersion.

The water-soluble or water-dispersible AMPS® copolymers according to the invention contain water-soluble ethylenically unsaturated monomers, hydrophobic monomers, or mixtures thereof.

The water-soluble co-monomers may be ionic or non-ionic.

Among the ionic water-soluble co-monomers, mention may be made, for example, of the following compounds and salts thereof:
(meth)acrylic acid,
styrenesulfonic acid,
vinylsulfonic acid and (meth)allylsulfonic acid,
vinylphosphonic acid,
maleic acid,
itaconic acid,
crotonic acid, water-soluble vinyl monomers of formula (A) below:

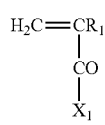

(A)

in which:
R$^1$ is chosen from H, —CH$_3$, —C$_2$H$_5$ and —C$_3$H$_7$;
X$_1$ is chosen from:
alkyl oxides of type —OR$_2$ where R$_2$ is a linear or branched, saturated or unsaturated hydrocarbon-based radical containing from 1 to 6 carbon atoms, substituted with at least one sulfonic (—SO$_3$—) and/or sulfate (—SO$_4$—) and/or phosphate (—PO$_4$H$_2$—) group.

Among the nonionic water-soluble co-monomers, mention may be made, for example, of:
(meth)acrylamide,
N-vinylacetamide and N-methyl-N-vinylacetamide,
N-vinylformamide and N-methyl-N-vinylformamide,
maleic anhydride,
vinylamine,
N-vinyllactams comprising a cyclic alkyl group containing from 4 to 9 carbon atoms, such as N-vinylpyrrolidone, N-butyrolactam and N-vinylcaprolactam,
vinyl alcohol of formula CH$_2$=CHOH,
water-soluble vinyl monomers of formula (B) below:

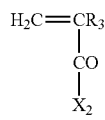

(B)

in which:
R$^3$ is chosen from H, —CH$_3$, —C$_2$H$_5$ and —C$_3$H$_7$;
X$_2$ is chosen from:
alkyl oxides of the type —OR$_4$ where R$_4$ is a linear or branched, saturated or unsaturated hydrocarbon-based radical having from 1 to 6 carbon atoms, optionally substituted with a halogen (iodine, bromine, chlorine or fluorine) atom; a hydroxyl (—OH) group; ether.

Mention is made, for example, of glycidyl (meth)acrylate, hydroxyethyl methacrylate, and (meth)acrylates of ethylene glycol, of diethylene glycol or of polyalkylene glycol.

Among the hydrophobic co-monomers without a fatty chain, mention may be made, for example, of:
styrene and derivatives thereof, such as 4-butylstyrene, α-methylstyrene and vinyltoluene;
vinyl acetate of formula CH$_2$=CH—OCOCH$_3$;
vinyl ethers of formula CH$_2$=CHOR in which R is a linear or branched, saturated or unsaturated hydrocarbon-based radical containing from 1 to 6 carbons;
acrylonitrile;
caprolactone;
vinyl chloride and vinylidene chloride;
silicone derivatives, which, after polymerization, result in silicone polymers such as methacryloxypropyltris(trimethylsiloxy)silane and silicone methacrylamides;

hydrophobic vinyl monomers of formula (C) below:

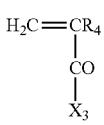

(C)

in which:
R$^4$ is chosen from H, —CH$_3$, —C$_2$H$_5$ and —C$_3$H$_7$;
X$_3$ is chosen from:
alkyl oxides of the type —OR$_5$ where R$_5$ is a linear or branched, saturated or unsaturated hydrocarbon-based radical containing from 1 to 6 carbon atoms.

Mention may be made, for example, of methyl methacrylate, ethyl methacrylate, n-butyl (meth)acrylate, tert-butyl (meth)acrylate, cyclohexyl acrylate, isobornyl acrylate and 2-ethylhexyl acrylate.

The water-soluble or water-dispersible AMPS® polymers of the invention preferably have a molar mass ranging from 50 000 g/mol to 10 000 000 g/mol, preferably from 80 000 g/mol to 8 000 000 g/mol, and even more preferably from 100 000 g/mol to 7 000 000 g/mol.

As water-soluble or water-dispersible AMPS homopolymers in accordance with the invention, mention may be made, for example, of crosslinked or non-crosslinked polymers of sodium acrylamido-2-methylpropanesulfonate, such as that used in the commercial product Simulgel 800 (CTFA name: Sodium Polyacryloyldimethyl Taurate), crosslinked ammonium acrylamido-2-methylpropanesulfonate polymers (INCI name: Ammonium polydimethyltauramide) such as those described in patent EP 0 815 928 B1 and such as the product sold under the trade name Hostacerin AMPS® by the company Clariant.

As water-soluble or water-dispersible AMPS copolymers in accordance with the invention, examples that may be mentioned include:
crosslinked acrylamide/sodium acrylamido-2-methylpropanesulfonate copolymers, such as that used in the commercial product Sepigel 305 (CTFA name: Polyacrylamide/C$_{13}$-C$_{14}$ Isoparaffin/Laureth-7) or that used in the commercial product sold under the name Simulgel 600 (CTFA name: Acrylamide/Sodium Acryloyldimethyltaurate/Isohexadecane/Poly sorbate-80) by the company SEPPIC;
copolymers of AMPS® and of vinylpyrrolidone or vinylformamide, such as that used in the commercial product sold under the name Aristoflex AVC® by the company Clariant (CTFA name: Ammonium acryloyldimethyltaurate/VP copolymer) but neutralized with sodium hydroxide or potassium hydroxide;
copolymers of AMPS® and of sodium acrylate, for instance the AMPS/sodium acrylate copolymer, such as that used in the commercial product sold under the name Simulgel EG® by the company SEPPIC or under the trade name Sepinov EM (CTFA name: Hydroxyethyl acrylate/sodium acryloyldimethyl taurate copolymer);
copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl acrylate/sodium acryloyldimethyltaurate copolymer (and) squalane (and) polysorbate 60), or such as the product sold under the name Sodium acrylamido-2-methylpropanesulfonate/hydroxyethyl acrylate copolymer, such as the commercial product Sepinov EMT 10 (INCI name: Hydroxyethyl acrylate/sodium acryloyldimethyl taurate copolymer).

Preferably, the product sold under the name Sodium acrylamido-2-methylpropanesulfonate/hydroxyethyl acrylate copolymer, such as the commercial product Sepinov EMT 10 (INCI name: Hydroxyethyl acrylate/sodium acryloyldimethyl taurate copolymer) is used as water-soluble or water-dispersible AMPS copolymers in accordance with the invention.

In general, an aqueous phase according to the invention may comprise from 0.1% to 8% by weight of solids, preferably 0.2% to 5% by weight, and more preferentially from 0.7% to 2.5% by weight of polyacrylamide(s) and of crosslinked and/or neutralized 2-acrylamido-2-methylpropanesulfonic acid polymer(s) and copolymer(s) relative to its total weight.

B.3 Modified or Unmodified Carboxyvinyl Polymers

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) comprising a hydrophobic group.

The term "copolymers" means both copolymers obtained from two types of monomer and those obtained from more than two types of monomer, such as terpolymers obtained from three types of monomer.

Their chemical structure more particularly comprises at least one hydrophilic unit and at least one hydrophobic unit. The term "hydrophobic group or unit" means a radical with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferably, these copolymers are chosen from copolymers derived from the polymerization:

of at least one monomer of formula (1) below:

$$CH_2 = \underset{R_2}{C} - \underset{O}{\overset{\|}{C}} - OH \qquad (1)$$

in which R1 denotes H or $CH_3$ or $C_2H_5$, i.e. acrylic acid, methacrylic acid or ethacrylic acid monomers, and of at least one monomer of unsaturated carboxylic acid ($C_{10}$-$C_{30}$)alkyl ester type corresponding to the monomer of formula (2) below:

$$CH_2 = \underset{R_2}{C} - \underset{O}{\overset{\|}{C}} - OR_3 \qquad (2)$$

in which $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical.

The unsaturated carboxylic acid ($C_{10}$-$C_{30}$)alkyl esters are preferably chosen from lauryl acrylate, stearyl acrylate, decyl acrylate, isodecyl acrylate and dodecyl acrylate, and the corresponding methacrylates, such as lauryl methacrylate, stearyl methacrylate, decyl methacrylate, isodecyl methacrylate and dodecyl methacrylate, and mixtures thereof.

According to a preferred embodiment, these polymers are crosslinked.

Among the copolymers of this type that will be used more particularly are polymers derived from the polymerization of a monomer mixture comprising:

essentially acrylic acid,
an ester of formula (2) described above in which R2 denotes H or $CH_3$, R3 denoting an alkyl radical containing from 12 to 22 carbon atoms,
(iii) and a crosslinking agent, which is a well-known copolymerizable polyethylenic unsaturated monomer, such as diallyl phthalate, allyl (meth)acrylate, divinylbenzene, (poly)ethylene glycol dimethacrylate or methylenebisacrylamide.

Among the copolymers of this type, use will more particularly be made of those consisting of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among the abovementioned polymers, the ones that are most particularly preferred according to the present invention are acrylate/$C_{10}$-$C_{30}$-alkyl acrylate copolymers (INCI name: Acrylates/$C_{10-30}$ Alkyl acrylate Crosspolymer) such as the products sold by the company Lubrizol under the trade names Pemulen TR-1, Pemulen TR-2, Carbopol 1382, Carbopol EDT 2020 and Carbopol Ultrez 20 Polymer, and even more preferentially Pemulen TR-2.

Among the modified or unmodified carboxyvinyl polymers, mention may also be made of sodium polyacrylates such as those sold under the name Cosmedia SP® containing 90% solids and 10% water, or Cosmedia SPL® as an inverse emulsion containing about 60% solids, an oil (hydrogenated polydecene) and a surfactant (PPG-5 Laureth-5), both sold by the company Cognis.

Mention may also be made of partially neutralized sodium polyacrylates that are in the form of a reverse emulsion comprising at least one polar oil, for example the product sold under the name Luvigel® EM sold by the company BASF.

The modified or unmodified carboxyvinyl polymers may also be chosen from crosslinked (meth)acrylic acid homopolymers.

For the purposes of the present patent application, the term "(meth)acrylic" means "acrylic or methacrylic".

Examples that may be mentioned include the products sold by Lubrizol under the names Carbopol 910, 934, 940, 941, 934 P, 980, 981, 2984, 5984 and Carbopol Ultrez 10 Polymer, or by 3V-Sigma under the name Synthalen® K, Synthalen® L or Synthalen® M.

Among the modified or unmodified carboxyvinyl polymers, mention may be made in particular of Carbopol (INCI name: carbomer) and Pemulen (CTFA name: Acrylates/C10-30 alkyl acrylate crosspolymer) sold by the company Lubrizol.

The modified or unmodified carboxyvinyl polymers may be present in a proportion of from 0.1% to 5% by weight of solids relative to the weight of the aqueous phase, in particular from 0.3% to 1% by weight and preferably in a proportion of about 1% by weight, relative to the weight of the aqueous phase.

According to a preferred variant, the hydrophilic gelling agent is chosen from crosslinked acrylic homopolymers or copolymers; associative polymers, in particular associative polymers of polyurethane type; polyacrylamides and crosslinked and/or neutralized 2-acrylamido-2-methylpropanesulfonic acid polymers and copolymers; modified or unmodified carboxyvinyl polymers, and mixtures thereof.

Advantageously, use is made, as synthetic polymeric hydrophilic gelling agent, of at least one gelling agent chosen from crosslinked acrylic homopolymers or copolymers; polyacrylamides and crosslinked and/or neutralized 2-acrylamido-2-methylpropanesulfonic acid polymers and copolymers; modified or unmodified carboxyvinyl polymers, and mixtures thereof, and preferentially at least one 2-acrylamido-2-methylpropanesulfonic acid polymer or copolymer, an associative polyurethane and/or a crosslinked sodium polyacrylate.

Lipophilic Gelling Agent For the purposes of the present patent application, the term "lipophilic gelling agent" means a compound that is capable of gelling the oily phase of the compositions according to the invention.

The gelling agent is lipophilic and is thus present in the oily phase of the composition.

The gelling agent is liposoluble or lipodispersible.

As emerges from the foregoing, the lipophilic gelling agent is advantageously chosen from particulate gelling agents, organopolysiloxane elastomers, semi-crystalline polymers and dextrin esters, and mixtures thereof.

I. Particulate Gelling Agents

The particulate gelling agent used in the composition according to the invention is in the form of particles, preferably spherical particles.

As representative lipophilic particulate gelling agents that are suitable for use in the invention, mention may be made most particularly of polar and apolar waxes, modified clays, and silicas such as fumed silicas and hydrophobic silica aerogels.

Waxes

The choice of a wax as lipophilic gelling agent is particularly advantageous for giving a composition according to the invention good emollience and comfort properties. Its combination with an aqueous phase gelled with a compound such as synthetic polymers gives access to compositions that have emollience and comfort with a fresh effect and advantageously an attenuated greasy feel. Compositions of this type are more particularly advantageous for dry to normal skin types.

The term "wax" under consideration in the context of the present invention generally means a lipophilic compound that is solid at room temperature (25° C.), with a solid/liquid reversible change of state, having a melting point of greater than or equal to 30° C., which may be up to 200° C. and in particular up to 120° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A 5 mg sample of wax placed in a crucible is subjected to a first temperature increase ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature of animal, vegetable, mineral or synthetic origin, and mixtures thereof.

For the purposes of the invention, the waxes may be those generally used in cosmetics or dermatology. They may especially be polar or apolar, and hydrocarbon-based, silicone and/or fluoro waxes, optionally comprising ester or hydroxyl functions. They may also be of natural or synthetic origin.

a) Apolar Waxes

For the purposes of the present invention, the term "apolar wax" means a wax whose solubility parameter at 25° C. as defined below, $\delta_a$, is equal to 0 $(J/cm^3)^{1/2}$.

The definition and calculation of the solubility parameters in the Hansen three-dimensional solubility space are described in the paper by C. M. Hansen: "*The three-dimensional solubility parameters*", J. Paint Technol., 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

Apolar waxes are in particular hydrocarbon waxes consisting solely of carbon and hydrogen atoms and devoid of heteroatoms, such as N, O, Si and P.

The apolar waxes are chosen from microcrystalline waxes, paraffin waxes, ozokerite and polyethylene waxes, and mixtures thereof.

Mention may be made, as ozokerite, of Ozokerite Wax SP 1020 P.

As microcrystalline waxes that may be used, mention may be made of

Multiwax W 445® sold by the company Sonneborn, and Microwax HW® and Base Wax 30540® sold by the company Paramelt, and Cerewax® No. 3 sold by the company Baerlocher.

As microwaxes that may be used in the compositions according to the invention as apolar wax, mention may be made especially of polyethylene microwaxes such as those sold under the names Micropoly 200®, 220®, 220L® and 250S® by the company Micro Powders.

Polyethylene waxes that may be mentioned include Performalene 500-L Polyethylene and Performalene 400 Polyethylene sold by New Phase Technologies, and Asensa® SC 211 sold by the company Honeywell.

b) Polar Wax

For the purposes of the present invention, the term "polar wax" means a wax whose solubility parameter at 25° C., $\delta_a$, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The polar waxes may especially be hydrocarbon-based, fluoro or silicone waxes.

Preferentially, the polar waxes may be hydrocarbon-based waxes.

The term "hydrocarbon-based wax" means a wax formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

According to the invention, the term "ester wax" means a wax comprising at least one ester function. According to the invention, the term "alcohol wax" means a wax comprising at least one alcohol functional group, i.e. comprising at least one free hydroxyl (OH) group.

The following may especially be used as ester wax:
ester waxes such as those chosen from:
i) waxes of formula $R_1COOR_2$ in which $R_1$ and $R_2$ represent linear, branched or cyclic aliphatic chains in which the number of atoms ranges from 10 to 50, which may contain a heteroatom such as O, N or P and whose melting point ranges from 25 to 120° C.;
ii) bis(1,1,1-trimethylolpropane) tetrastearate, sold under the name Hest 2T-4S® by the company Heterene;
iii) diester waxes of a dicarboxylic acid of general formula $R^3$—(—OCO—$R^4$—COO—$R^5$), in which $R^3$ and $R^5$ are identical or different, preferably identical and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups, and preferably that is linear and unsaturated;
iv) mention may also be made of the waxes obtained by catalytic hydrogenation of animal or plant oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol;
v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax and hydrogenated jojoba wax, sunflower wax, lemon wax, olive wax or berry wax.

According to another embodiment, the polar wax can be an alcohol wax. According to the invention, the term "alcohol wax" means a wax comprising at least one alcohol function, i.e. comprising at least one free hydroxyl (OH) group. Examples of alcohol waxes that may be mentioned include the wax C30-50 Alcohols Performacol® 550 Alcohol sold by the company New Phase Technologies, stearyl alcohol and cetyl alcohol.

It is also possible to use silicone waxes, which may advantageously be substituted polysiloxanes, preferably of low melting point.

The term "silicone wax" means a wax comprising at least one silicon atom, and especially comprising Si—O groups.

Among the commercial silicone waxes of this type, mention may be made especially of those sold under the names Abilwax 9800, 9801 or 9810 (Goldschmidt), KF910 and KF7002 (Shin-Etsu), or 176-1118-3 and 176-11481 (General Electric).

The silicone waxes that may be used may also be alkyl or alkoxy dimethicones, and also ($C_{20}$-$C_{60}$)alkyl dimethicones, in particular ($C_{30}$-$C_{45}$)alkyl dimethicones, such as the silicone wax sold under the name SF-1642 by the company GE-Bayer Silicones or C30-45 alkyl dimethylsilyl polypropylsilsesquioxane sold under the name SW-8005® C30 Resin Wax by the company Dow Corning.

In the context of the present invention, particularly advantageous waxes that may be mentioned include polyethylene waxes, jojoba wax, candelilla wax and silicone waxes, in particular candelilla wax.

They may be present in the oily phase in a proportion of from 0.5% to 30% by weight relative to the weight of the oily phase, for example between 5% and 20% of the oily phase and more particularly from 2% to 15% by weight relative to the weight of the oily phase.

Modified Clays

The composition according to the invention may comprise at least one lipophilic clay.

The clays may be natural or synthetic, and they are made lipophilic by treatment with an alkylammonium salt such as a $C_{10}$ to $C_{22}$ ammonium chloride, for example distearyldimethylammonium chloride.

They may be chosen from bentonites, in particular hectorites and montmorillonites, beidellites, saponites, nontronites, sepiolites, biotites, attapulgites, vermiculites and zeolites.

They are preferably chosen from hectorites.

Hectorites modified with a $C_{10}$ to $C_{22}$ ammonium chloride, for instance hectorite modified with distearyldimethylammonium chloride, for instance the product sold under the name Bentone 38V® by the company Elementis or bentone gel in isododecane sold under the name Bentone Gel ISD V® (87% isododecane/10% disteardimonium hectorite/3% propylene carbonate) by the company Elementis, are preferably used as lipophilic clays.

Lipophilic clay may especially be present in a content ranging from 0.1% to 15% by weight, particularly from 0.5% to 10% and more particularly from 1% to 10% by weight relative to the total weight of the oily phase.

Silicas

The oily phase of a composition according to the invention may also comprise, as gelling agent, a fumed silica or silica aerogel particles.

a) Fumed Silica

Fumed silica which has undergone a hydrophobic surface treatment is most particularly suitable for use in the invention. Specifically, it is possible to chemically modify the surface of silica, by chemical reaction generating a reduced number of silanol groups present at the surface of the silica. Silanol groups can in particular be replaced by hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as "silica silylate" according to the CTFA (8th edition, 2000). They are sold, for example, under the references Aerosil R812® by the company Degussa, and Cab-O-Sil TS-530® by the company Cabot;

dimethylsilyloxyl or polydimethylsiloxane groups, which are obtained in particular by treating fumed silica in the presence of polydimethylsiloxane or dimethyldichlorosilane. Silicas thus treated are named "Silica dimethyl silylate" according to the CTFA (8th edition, 2000). They are, for example, sold under the references Aerosil R972® and Aerosil R974® by the company Degussa and Cab-O-Sil TS-610® and Cab-O-Sil TS-720® by the company Cabot.

The fumed silicas may be present in a composition according to the present invention in a content of between 0.1% and 40% by weight, more particularly between 1% and 15% by weight and even more particularly between 2% and 10% by weight relative to the total weight of the oily phase.

B) Hydrophobic Silica Aerogels

The oily phase of a composition according to the invention may also comprise, as gelling agent, at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid the contraction of the pores and of the material. The sol-gel process and the various drying operations are described in detail in Brinker C. J. and Scherer G. W., Sol-Gel Science, New York: Academic Press, 1990.

The hydrophobic silica aerogel particles used in the present invention have a specific surface area per unit of mass (SM) ranging from 500 to 1500 m²/g, preferably from 600 to 1200 m²/g and better still from 600 to 800 m²/g, and a size expressed as the volume-mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles used in the present invention have a size expressed as volume-mean diameter (D[0.5]) ranging from 1 to 30 μm, preferably from 5 to 25 μm, better still from 5 to 20 μm and even better still from 5 to 15 μm.

The specific surface area per unit of mass can be determined by the nitrogen adsorption method, known as the BET (Brunauer-Emmett-Teller) method, described in the Journal of the American Chemical Society, Vol. 60, page 309, February 1938, which corresponds to international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., *Light Scattering by Small Particles*, Chapters 9 and 10, Wiley, New York, 1957.

According to an advantageous embodiment, the hydrophobic silica aerogel particles used in the present invention have a specific surface area per unit of mass (SM) ranging from 600 to 800 m²/g.

The silica aerogel particles used in the present invention may advantageously have a tapped density ρ ranging from 0.02 g/cm³ to 0.10 g/cm³, preferably from 0.03 g/cm³ to 0.08 g/cm³ and in particular ranging from 0.05 g/cm³ to 0.08 g/cm³.

In the context of the present invention, this density may be assessed according to the following protocol, known as the tapped density protocol:

40 g of powder are poured into a measuring cylinder; the measuring cylinder is then placed on a Stay 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in cm³ and m in g).

According to one embodiment, the hydrophobic silica aerogel particles used in the present invention have a specific surface area per unit of volume SV ranging from 5 to 60 m²/cm³, preferably from 10 to 50 m²/cm³ and better still from 15 to 40 m²/cm³.

The specific surface area per unit of volume is given by the relationship: $S_V=S_M \times \rho$; where ρ is the tapped density, expressed in g/cm³, and $S_M$ is the specific surface per unit of mass, expressed in m²/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorbing capacity measured at the wet point, noted Wp, corresponds to the amount of oil that needs to be added to 100 g of particles in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. From this point, the oil is added one drop at a time and the mixture is then triturated with the spatula. The addition of oil is stopped when a firm, smooth paste is obtained. This paste must be able to be spread over the glass plate without cracks or the formation of lumps. The volume Vs (expressed in ml) of oil used is then noted.

The oil uptake corresponds to the ratio Vs/m.

The aerogels used according to the present invention are aerogels of hydrophobic silica, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will preferably be made of hydrophobic silica aerogel particles surface-modified with trimethylsilyl groups, preferably of the INCI name Silica silylate.

As hydrophobic silica aerogels that may be used in the invention, examples that may be mentioned include the aerogel sold under the name VM-2260 or VM-2270 (INCI name: Silica silylate), by the company Dow Corning, the particles of which have an average size of about 1000 microns and a specific surface area per unit of mass ranging from 600 to 800 $m^2/g$.

Mention may also be made of the aerogels sold by the company Cabot under the references Aerogel TLD 201, Aerogel OGD 201 and Aerogel TLD 203, Enova® Aerogel MT 1100 and Enova Aerogel MT 1200.

Use will preferably be made of the aerogel sold under the name VM-2270 (INCI name: Silica silylate), by the company Dow Corning, the particles of which have an average size ranging from 5-15 microns and a specific surface area per unit of mass ranging from 600 to 800 $m^2/g$.

Preferably, the hydrophobic silica aerogel particles are present in the composition according to the invention in a solids content ranging from 0.1% to 8% by weight, preferably from 0.2% to 5% by weight and preferably from 0.2% to 3% by weight relative to the total weight of the oily phase.

The choice of a silicon derivative or of a modified clay as lipophilic gelling agent proves to be more particularly favoured for preparing cosmetic compositions intended for affording a mattifying and non-greasy effect with a freshness effect.

Such a gelling agent is particularly advantageous for formulating care and/or makeup compositions intended for greasy to combination skin types.

II. Organopolysiloxane Elastomer

The organopolysiloxane elastomer that may be used as lipophilic gelling agent also has the advantage of giving the composition according to the invention good application properties. It affords a very gentle feel and a matte effect after application, which is advantageous especially for application to the skin, in particular for foundation compositions. It may also allow efficient filling of the hollows present on keratin materials.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

Compound (A) is the base compound for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) can exhibit any molecular structure, in particular a linear chain or branched chain structure or a cyclic structure.

Compound (A) can have a viscosity at 25° C. ranging from 1 to 50 000 centistokes, in particular in order to be satisfactorily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) can thus be chosen from methylhydrogenopolysiloxanes comprising trimethylsiloxy end groups, dimethylsiloxane-methylhydrosiloxane copolymers comprising trimethylsiloxy end groups, and dimethyl siloxane-methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups can be located at any position on the organopolysiloxane molecule but are preferably located at the ends of the organopolysiloxane molecule. The organopolysiloxane (B) can have a branched-chain, linear-chain, cyclic or network structure but the linear-chain structure is preferred. The compound (B) can have a viscosity ranging from the liquid state to the gum state. Preferably, the compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinyl siloxy end groups, dimethyl siloxane-diphenyl siloxane-methylvinyl siloxane copolymers comprising dimethylvinylsiloxy end groups, dimethylsiloxane-methylvinylsiloxane copolymers comprising trimethylsiloxy end groups, dimethyl siloxane-methylphenyl siloxane-methylvinyl siloxane copolymers comprising trimethyl siloxy end groups, methyl(3,3,3-trifluoropropyl)polysiloxanes comprising dimethylvinyl siloxy end groups, and dimethylsiloxane-methyl(3,3,3-trifluoropropyl)siloxane copolymers comprising dimethylvinylsiloxy end groups.

In particular, the organopolysiloxane elastomer can be obtained by reaction of dimethylpolysiloxane comprising dimethylvinylsiloxy end groups and of methylhydropolysiloxane comprising trimethylsiloxy end groups, in the presence of a platinum catalyst.

Advantageously, the sum of the number of ethylene groups per molecule of compound (B) and of the number of hydrogen atoms bonded to silicon atoms per molecule of compound (A) is at least 5.

It is advantageous for compound (A) to be added in an amount such that the molecular ratio of the total amount of hydrogen atoms bonded to silicon atoms in compound (A) to the total amount of all the ethylenically unsaturated groups in compound (B) is within the range from 1.5/1 to 20/1.

Compound (C) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

The catalyst (C) is preferably added from 0.1 to 1000 parts by weight, better still from 1 to 100 parts by weight, as platinum metal proper, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular mode of the invention, the composition comprises an organopolysiloxane elastomer free of polyoxyalkylene units and of polyglyceryl units.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name).

The organopolysiloxane elastomer particles may be conveyed in the form of a gel formed from an elastomeric organopolysiloxane included in at least one hydrocarbon-based oil and/or one silicone oil. In these gels, the organopolysiloxane particles are often nonspherical particles.

Non-emulsifying elastomers are described especially in patents EP 242 219, EP 285 886 and EP 765 656 and in patent application JP-A-61-194009, the content of which is incorporated herein by way of reference.

The silicone elastomer is generally in the form of a gel, a paste or a powder, but advantageously in the form of a gel in which the silicone elastomer is dispersed in a linear silicone oil (dimethicone) or cyclic silicone oil (e.g.: cyclopentasiloxane), advantageously in a linear silicone oil.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

According to another alternative, the composition according to the invention may comprise an organopolysiloxane elastomer having the INCI name 'Polysilicone 11', such as those sold under the name Gransil by Grant Industries.

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, optionally modified with optionally fluorinated aliphatic groups, or with functional groups such as hydroxyl, thiol and/or amine groups.

Mention may be made especially of the compounds having the following INCI names:
Dimethicone/Vinyl Dimethicone Crosspolymer, such as USG-105 and USG-107A from the company Shin-Etsu; DC9506 and DC9701 from the company Dow Corning,
dimethicone/vinyl dimethicone crosspolymer (and) dimethicone, such as KSG-6 and KSG-16 from the company Shin-Etsu;
dimethicone/vinyl dimethicone crosspolymer (and) cyclopentasiloxane, such as KSG-15,
cyclopentasiloxane (and) dimethicone crosspolymer, such as DC9040, DC9045 and DC5930 from the company Dow Corning,
dimethicone (and) dimethicone crosspolymer, such as DC9041 from the company Dow Corning,
dimethicone (and) dimethicone crosspolymer, such as Dow Corning EL-9240® silicone elastomer blend from the company Dow Corning (mixture of polydimethylsiloxane crosslinked with hexadiene/polydimethylsiloxane (2 cSt)),
$C_{4-24}$ alkyl dimethicone/divinyl dimethicone crosspolymer, such as NuLastic Silk MA from the company Alzo.

As examples of silicone elastomers dispersed in a linear silicone oil that may advantageously be used according to the invention, mention may especially be made of the following references:
dimethicone/vinyl dimethicone crosspolymer (and) dimethicone, such as KSG-6 and KSG-16 from the company Shin-Etsu;
dimethicone (and) dimethicone crosspolymer, such as DC9041 from the company Dow Corning; and
dimethicone (and) dimethicone crosspolymer, such as Dow Corning EL-9240® silicone elastomer blend from the company Dow Corning.

According to a preferred embodiment, the composition according to the invention comprises at least one crosslinked silicone elastomer having the INCI name 'dimethicone crosspolymer' or 'dimethicone (and) dimethicone crosspolymer', with preferably a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 Dow Corning or the mixture of polydimethylsiloxane crosslinked with hexadiene/polydimethylsiloxane (2 cSt) sold under the name Dow Corning EL-9240® silicone elastomer blend Dow Corning.

According to a particularly preferred embodiment, the composition according to the invention comprises at least one crosslinked silicone elastomer having the INCI name 'dimethicone (and) dimethicone crosspolymer', with preferably a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 Dow Corning.

The organopolysiloxane elastomer particles may also be used in powder form: mention may be made of the powders sold under the names Dow Corning 9505 Powder and Dow Corning 9506 Powder by the company Dow Corning, these powders having the INCI name: dimethicone/vinyl dimethicone crosspolymer.

The organopolysiloxane powder may also be coated with silsesquioxane resin, as described, for example, in patent U.S. Pat. No. 5,538,793. Such elastomeric powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

As preferred lipophilic gelling agents of organopolysiloxane elastomer type, mention may be made more particularly of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), and in particular mention be made of Dimethicone Crosspolymer (INCI name).

The organopolysiloxane elastomer may be present in a composition according to the present invention in a content of between 0.5% and 35% by weight of solids and especially between 2% and 15% by weight relative to the total weight of the oily phase.

III. Semicrystalline Polymers

The composition according to the invention may comprise at least one semi-crystalline polymer. Preferably, the semi-crystalline polymer has an organic structure, and a melting point of greater than or equal to 30° C.

For the purposes of the invention, the term "semi-crystalline polymer" means polymers comprising a crystallizable portion and an amorphous portion and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is preferably greater than or equal to 30° C. and less than 70° C.

The semi-crystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5° C. or 10° C. per minute. (The melting point under consideration is the point corresponding to the temperature of the most endothermic peak of the thermogram).

The semi-crystalline polymer(s) according to the invention preferably have a melting point that is higher than the temperature of the keratinous support intended to receive the said composition, in particular the skin or the lips.

According to the invention, the semi-crystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which is pendent or lateral relative to the polymer backbone. A block is a group of atoms belonging to the backbone, this group constituting one of the repeating units of the polymer.

Preferably, the polymer backbone of the semi-crystalline polymers is soluble in the fatty phase at a temperature above their melting point.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers having crystallizable side chains, these side chains are advantageously in random or statistical form.

Preferably, the semi-crystalline polymers of the invention are of synthetic origin.

According to a preferred embodiment, the semi-crystalline polymer is chosen from:
  homopolymers and copolymers comprising units resulting from the polymerization of one or more monomers bearing crystallizable hydrophobic side chain(s),
  polymers bearing in the backbone at least one crystallizable block,
  polycondensates of aliphatic or aromatic or aliphatic/aromatic polyester type,
  copolymers of ethylene and propylene prepared via metallocene catalysis, and
  acrylate/silicone copolymers.

The semi-crystalline polymers that may be used in the invention may be chosen in particular from:
  block copolymers of polyolefins of controlled crystallization, whose monomers are described in EP-A-0 951 897,
  polycondensates, especially of aliphatic or aromatic or aliphatic/aromatic polyester type,
  copolymers of ethylene and propylene prepared via metallocene catalysis,
  homopolymers or copolymers bearing at least one crystallizable side chain and homopolymers or copolymers bearing in the backbone at least one crystallizable block, such as those described in document U.S. Pat. No. 5,156,911, such as the $(C_{10}\text{-}C_{30})$alkyl polyacrylates corresponding to the Intelimer® products from the company Landec described in the brochure *Intelimer® Polymers*, Landec 1P22 (Rev. 4-97), for example the product Intelimer® IPA 13-1 from the company Landec, which is a polystearyl acrylate with a molecular weight of about 145 000 and a melting point of 49° C., homopolymers or copolymers bearing at least one crystallizable side chain, in particular containing fluoro group(s), as described in document WO-A-01/19333, acrylate/silicone copolymers, such as copolymers of acrylic acid and of stearyl acrylate bearing polydimethylsiloxane grafts, copolymers of stearyl methacrylate bearing polydimethylsiloxane grafts, copolymers of acrylic acid and of stearyl methacrylate bearing polydimethylsiloxane grafts, copolymers of methyl methacrylate, butyl methacrylate, 2-ethylhexyl acrylate and stearyl methacrylate bearing polydimethylsiloxane grafts. Mention may be made in particular of the copolymers sold by the company Shin-Etsu under the names KP-561 (CTFA name: acrylates/dimethicone), KP-541 (CTFA name: acrylates/dimethicone and isopropyl alcohol), KP-545 (CTFA name: acrylates/dimethicone and cyclopentasiloxane), and mixtures thereof.

Preferably, the amount of semi-crystalline polymer(s), preferably chosen from semi-crystalline polymers bearing crystallizable side chains, represents from 0.1% to 30% by weight of solids relative to the total weight of the oily phase, for example from 0.5% to 25% by weight, better still from 5% to 20% or even from 5% to 12% by weight, relative to the total weight of the oily phase.

IV. Dextrin Esters

The composition according to the invention may comprise as lipophilic gelling agent at least one dextrin ester.

In particular, the composition preferably comprises at least one preferably $C_{12}$ to $C_{24}$ and in particular $C_{14}$-$C_{18}$ fatty acid ester of dextrin, or mixtures thereof.

Preferably, the dextrin ester is an ester of dextrin and of a $C_{12}$-$C_{18}$ and in particular $C_{14}$-$C_{18}$ fatty acid.

Preferably, the dextrin ester is chosen from dextrin myristate and/or dextrin palmitate, and mixtures thereof.

According to a particular embodiment, the dextrin ester is dextrin myristate, especially such as the product sold especially under the name Rheopearl MKL-2 by the company Chiba Flour Milling.

According to a preferred embodiment, the dextrin ester is dextrin palmitate. This product may be chosen, for example, from those sold under the names Rheopearl TL®, Rheopearl KL® and Rheopearl® KL2 by the company Chiba Flour Milling.

In a particularly preferred manner, the oily phase of a composition according to the invention may comprise from 0.1% to 30% by weight, preferably from 2% to 25% and preferably from 7.5% to 17% by weight of dextrin ester(s) relative to the total weight of the oily phase.

In a particularly preferred manner, the composition according to the invention may comprise between 0.1% and 10% by weight and preferably between 0.5% and 5% by weight of dextrin palmitate relative to the total weight of the oily phase. The dextrin palmitate may especially be the product sold under the names Rheopearl TL®, Rheopearl KL® or Rheopearl® KL2 by the company Chiba Flour Milling.

According to an advantageous variant, a composition according to the invention comprises a lipophilic gelling agent chosen from modified clays and especially bentonites and preferably hectorites; waxes, in particular polar waxes especially including ester waxes and preferably candelilla wax; hydrophobic silica, in particular hydrophobic silica aerogels and preferably silica silylates; dextrin esters and preferably dextrin palmitate, organopolysiloxane elastomers, and mixtures thereof.

In particular, this lipophilic gelling agent is chosen from at least one organopolysiloxane elastomer or a dextrin ester and/or a particulate gelling agent, and in particular is chosen from a hydrophobic silica, a modified clay and a wax, and mixtures thereof.

Hydrophilic Gelling Agent(s)/Lipophilic Gelling Agent(s) Systems

As preferred synthetic polymeric hydrophilic gelling agents, mention may be made more particularly of:

a) 2-acrylamido-2-methylpropanesulfonic acid polymers, for instance AMPS® and 2-acrylamido-2-methylpropanesulfonic acid copolymers and in particular copolymers of AMPS® and of hydroxyethyl acrylate, for instance the AMPS®/hydroxyethyl acrylate copolymer such as that used in the commercial product sold under the name Simulgel NS® by the company SEPPIC (CTFA name: Hydroxyethyl acrylate/sodium acryloyldimethyltaurate copolymer (and) squalane (and) polysorbate 60), or such as the product sold under the name Sodium acrylamido-2-methylpropanesulfonate/hydroxyethyl acrylate copolymer, such as the commercial product Sepinov EMT 10 (INCI name: Hydroxyethyl acrylate/sodium acryloyldimethyl taurate copolymer);

b) associative polymers, in particular nonionic associative polymers especially of polyurethane type, for instance associative polyurethanes, such as Steareth-100/PEG-136/HDI Copolymer sold under the name Rheolate FX 1100 by Elementis;

c) crosslinked acrylic homopolymers or copolymers, and in particular crosslinked sodium polyacrylates, for instance Aquakeep from the company Sumitomo Seika;

d) modified or unmodified carboxyvinyl polymers, and in particular Pemulen (CTFA name: Acrylates/C10-30 alkyl acrylate crosspolymer) sold by the company Lubrizol, and also those made of sodium polyacrylates such as those sold under the name Cosmedia SP® containing 90% solids and 10% water, by the company Cognis.

As preferred lipophilic gelling agents of organopolysiloxane elastomer type, mention may be made more particularly of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), and in particular mention be made of Dimethicone Crosspolymer (INCI name) and Dimethicone (and) Dimethicone Crosspolymer (INCI name).

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, especially the following references:

dimethicone/vinyl dimethicone crosspolymer (and) dimethicone, such as KSG-6 and KSG-16 from the company Shin-Etsu;

dimethicone (and) dimethicone crosspolymer, such as DC9041 from the company Dow Corning; and dimethicone (and) dimethicone crosspolymer (INCI name), such as Dow Corning EL-9240® silicone elastomer blend from the company Dow Corning.

According to a particularly preferred embodiment, the composition according to the invention comprises at least one crosslinked silicone elastomer having the INCI name 'dimethicone (and) dimethicone crosspolymer', with preferably a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 Dow Corning or the mixture of polydimethylsiloxane crosslinked with hexadiene/polydimethylsiloxane (2 cSt) sold under the name Dow Corning EL-9240® silicone elastomer blend from Dow Corning.

As preferred lipophilic particulate gelling agent(s), mention may be made more particularly of:

a) modified clays and especially bentonites and preferably hectorites. Especially suitable for use in this respect are Bentone 38V and the gel of Bentone in isododecane under the name Bentone Gel ISD V® sold by the company Elementis;

b) waxes, in particular polar waxes especially including ester waxes such as candelilla wax;

c) hydrophobic silica, in particular hydrophobic silica aerogels such as silica silylates, in particular those sold under the name VM-2270 (INCI name: Silica silylate) by the company Dow Corning.

Thus, a composition according to the invention may advantageously comprise as lipophilic gelling agent at least one organopolysiloxane elastomer or a dextrin ester and/or a particulate gelling agent, in particular chosen from a hydrophobic silica, a modified clay and a wax, and mixtures thereof.

As non-limiting illustrations of hydrophilic gelling agent(s)/lipophilic gelling agent(s) systems that are most particularly suitable for use in the invention, mention may be made especially of the following systems:

polymers or copolymers of 2-acrylamido-2-methylpropanesulfonic acid/organopolysiloxane elastomer(s) and/or particulate lipophilic gelling agent(s);

associative polymer especially of polyurethane/particulate lipophilic gelling agent(s) type;

associative polymer especially of polyurethane and/or modified or unmodified carboxyvinyl polymers/particulate lipophilic gelling agent(s) type;

polymers or copolymers of 2-acrylamido-2-methylpropanesulfonic acid and/or associative polymer especially of polyurethane/organopolysiloxane elastomer(s);

modified or unmodified carboxyvinyl polymers/particulate lipophilic gelling agent(s) type; and modified or unmodified carboxyvinyl polymers/organopolysiloxane elastomer(s).

Thus, a composition according to the invention may advantageously comprise as hydrophilic gelling agent(s)/lipophilic gelling agent(s) systems, a system chosen from:

copolymer of 2-acrylamido-2-methylpropanesulfonic acid and of hydroxyethyl acrylate/organopolysiloxane elastomer;

polymer of 2-acrylamido-2-methylpropanesulfonic acid combined with a crosslinked sodium polyacrylate/hydrophobic silica combined with an organopolysiloxane elastomer;

copolymer of 2-acrylamido-2-methylpropanesulfonic acid and of hydroxyethyl acrylate/modified clay;

copolymer of 2-acrylamido-2-methylpropanesulfonic acid and of hydroxyethyl acrylate/dextrin ester and wax;

associative polyurethane/modified clay;

copolymer of 2-acrylamido-2-methylpropanesulfonic acid and of hydroxyethyl acrylate/polar wax;

associative polyurethane/wax;

acrylate/$C_{10}$-$C_{30}$-alkyl acrylate copolymer combined with an associative polyurethane/modified clay;

copolymer of 2-acrylamido-2-methylpropanesulfonic acid and of hydroxyethyl acrylate combined with an associative polyurethane/organopolysiloxane elastomer;

copolymer of 2-acrylamido-2-methylpropanesulfonic acid and of hydroxyethyl acrylate/hydrophobic silica combined with an organopolysiloxane elastomer-polymer of 2-acrylamido-2-methylpropanesulfonic acid/organopolysiloxane elastomer;

polymer of 2-acrylamido-2-methylpropanesulfonic acid/modified clay;

modified or unmodified carboxyvinyl polymers made of sodium polyacrylates/organopolysiloxane elastomer; and modified or unmodified carboxyvinyl polymers made of sodium polyacrylates/modified clay.

Advantageously, the organopolysiloxane elastomer under consideration as lipophilic gelling agent is chosen from Dimethicone Crosspolymer, Dimethicone (and) Dimethicone Crosspolymer, Vinyl Dimethicone Crosspolymer, Dimethicone/Vinyl Dimethicone Crosspolymer and Dimethicone Crosspolymer-3.

Aqueous Phase

The aqueous phase of a composition according to the invention comprises water and optionally a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the composition in a content ranging from 5% to 95%, better still from 30% to 80% by weight and preferably from 40% to 75% by weight relative to the total weight of the said composition.

According to another embodiment variant, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols advantageously suitable for the formulation of a composition according to the present invention are those exhibiting in particular from 2 to 32 carbon atoms and preferably from 3 to 16 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols such as glycerol oligomers, for instance diglycerol, and polyethylene glycols, and mixtures thereof.

According to a preferred embodiment of the invention, the said polyol is chosen from ethylene glycol, pentaerythritol, trimethylolpropane, propylene glycol, glycerol, polyglycerols and polyethylene glycols, and mixtures thereof.

According to a particular embodiment, the composition of the invention may comprise at least propylene glycol.

According to another particular embodiment, the composition of the invention may comprise at least glycerol.

Oily Phase

For the purposes of the invention, an oily phase comprises at least one oil.

The term "oil" means any fatty substance that is in liquid form at room temperature and atmospheric pressure.

An oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They can be of animal, vegetable, mineral or synthetic origin. According to one embodiment variant, oils of plant origin are preferred.

For the purposes of the present invention, the term "non-volatile oil" means an oil with a vapour pressure of less than 0.13 Pa.

For the purposes of the present invention, the term "silicone oil" is intended to mean an oil comprising at least one silicon atom, and in particular at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a nonzero vapour pressure, at room temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1,300 Pa (0.01 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched $C_8$-$C_{16}$ alkanes, for instance $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, for instance isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for instance n-dodecane (C12) and n-tetradecane (C14) sold by Sasol under the respective references Parafol 12-97 and Parafol 14-97, and also mixtures thereof, the undecane-tridecane mixture, mixtures of n-undecane ($C_{11}$) and of n-tridecane ($C_{13}$) obtained in Examples 1 and 2 of patent application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane and dodecamethylcyclohexasiloxane.

Non-Volatile Oils

The non-volatile oils may be chosen especially from non-volatile hydrocarbon-based, fluoro and/or silicone oils.

Non-volatile hydrocarbon-based oils that may especially be mentioned include:
  hydrocarbon-based oils of animal origin,
  hydrocarbon-based oils of plant origin, synthetic ethers containing from 10 to 40 carbon atoms, such as dicapryl ether,
  synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty alcohol and fatty acid esters, for instance cetostearyl octanoate, isopropyl alcohol esters such as isopropyl myristate or isopropyl palmitate, ethyl palmitate, 2-ethylhexyl palmitate, isopropyl stearate, octyl stearate, hydroxylated esters, for instance isostearyl lactate or octyl hydroxystearate, alkyl or polyalkyl ricinoleates, hexyl laurate, neopentanoic acid esters, for instance isodecyl neopentanoate or isotridecyl neopentanoate, and isononanoic acid esters, for instance isononyl isononanoate or isotridecyl isononanoate,
  polyol esters and pentaerythritol esters, for instance dipentaerythrityl tetrahydroxystearate/tetraisostearate,
  fatty alcohols that are liquid at room temperature, with a branched and/or unsaturated carbon-based chain containing from 12 to 26 carbon atoms, for instance 2-octyldodecanol, isostearyl alcohol and oleyl alcohol,
  $C_{12}$-$C_{22}$ higher fatty acids, such as oleic acid, linoleic acid, linolenic acid, and mixtures thereof,
  non-phenyl silicone oils, for instance caprylyl methicone, and
  phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenyl ethyl trimethylsiloxysilicates, dimethicones or phenyl trimethicone with a viscosity of less than or equal to 100 cSt, and trimethyl pentaphenyl trisiloxane, and mixtures thereof; and also mixtures of these various oils.

Preferably, a composition according to the invention comprises volatile and/or non volatile silicone oils. Such silicone oils are particularly appreciated when the oily gelling agent is an organopolysiloxane polymer.

A composition according to the invention may comprise from 5% to 95% by weight, better still from 5% to 40% by weight and preferably from 7% to 35% by weight of oil(s) relative to the total weight of the said composition.

As mentioned above, the gelled oily phase according to the invention may have a threshold stress of greater than 1.5 Pa and preferably greater than 10 Pa. This threshold stress value reflects a gel-type texture of this oily phase.

Dyestuffs

A composition according to the invention may also comprise at least one particulate or non-particulate, water-soluble or water-insoluble dyestuff, preferably in a proportion of at least 0.01% by weight relative to the total weight of the composition.

For obvious reasons, this amount is liable to vary significantly with regard to the intensity of the desired colour effect and of the colour intensity afforded by the dyestuffs under consideration, and its adjustment clearly falls within the competence of a person skilled in the art.

A composition according to the invention may comprise from 0.01% to 15% by weight, especially from 0.1% to 15% by weight, in particular from 1% to 15% by weight and preferably from 5% to 15% by weight of dyestuffs relative to the total weight of the said composition.

Advantageously, a composition according to the invention may comprise from 0.01% to 25% by weight, especially from 0.1% to 25% by weight, in particular from 1% to 20% by weight and preferably from 5% to 15% by weight of dyestuffs relative to the total weight of the said composition.

As stated above, the dyestuffs that are suitable for use in the invention may be water-soluble, but may also be liposoluble.

For the purposes of the invention, the term "water-soluble dyestuff" means any natural or synthetic, generally organic compound, which is soluble in an aqueous phase or water-miscible solvents and which is capable of imparting colour.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanin (beetroot), carmine, copper chlorophylline, methylene blue, anthocyanins (enocianin, black carrot, hibiscus and elder), caramel and riboflavin.

The water-soluble dyes are, for example, beetroot juice and caramel.

For the purposes of the invention, the term "liposoluble dyestuff" means any natural or synthetic, generally organic compound, which is soluble in an oily phase or in solvents that are miscible with a fatty substance, and which is capable of imparting colour.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

The particulate dyestuffs may be present in a proportion of from 0.01% to 15% by weight relative to the total weight of the composition containing them.

They may especially be pigments, nacres and/or particles with metallic tints.

The term "pigments" should be understood as meaning white or coloured, mineral or organic particles that are insoluble in an aqueous solution, which are intended to colour and/or opacify the composition containing them.

Advantageously, a composition according to the invention may comprise from 0.01% to 25% by weight, especially from 0.1% to 25% by weight, in particular from 1% to 20% by weight and preferably from 5% to 15% by weight of pigments relative to the total weight of the said composition.

Preferably, when a composition according to the invention is a make-up composition, it may comprise at least 5%, and more preferably at least 10% by weight of pigments relative to the total weight of the said composition.

The pigments may be white or coloured, and mineral and/or organic.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term "nacres" should be understood as meaning iridescent or non-iridescent coloured particles of any shape, especially produced by certain molluscs in their shell or alternatively synthesized, which have a colour effect via optical interference.

A composition according to the invention may comprise from 0 to 15% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

Advantageously, the nacres in accordance with the invention are micas coated with titanium dioxide or with iron oxide, and also bismuth oxychloride.

For the purposes of the present invention, the term "particles with a metallic tint" means any compound whose nature, size, structure and surface finish allow it to reflect the incident light, especially in a non-iridescent manner.

The particles with a metallic tint that may be used in the invention are in particular chosen from:
- particles of at least one metal and/or of at least one metal derivative;
- particles comprising a monomaterial or multimaterial organic or mineral substrate, at least partially coated with at least one layer with a metallic tint comprising at least one metal and/or at least one metal derivative; and
- mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" denotes compounds derived from metals, especially oxides, fluorides, chlorides and sulfides.

Illustrations of these particles that may be mentioned include aluminum particles, such as those sold under the names Starbrite 1200 EAC® by the company Siberline and Metalure® by the company Eckart and glass particles coated with a metallic layer, especially those described in documents JP-A-09188830, JP-A-10158450, JP-A-10158541, JP-A-07258460 and JP-A-05017710.

Hydrophobic Treatment of the Dyestuffs

The pulverulent dyestuffs as described previously may be totally or partially surface-treated, with a hydrophobic agent, to make them more compatible with the oily phase of the composition of the invention, especially so that they have good wettability with oils. Thus, these treated pigments are well dispersed in the oily phase.

Hydrophobic-treated pigments are described especially in document EP-A-1 086 683.

The hydrophobic-treatment agent may be chosen from silicones such as methicones, dimethicones and perfluoroalkylsilanes; fatty acids, for instance stearic acid; metal soaps, for instance aluminium dimyristate, the aluminium salt of hydrogenated tallow glutamate; perfluoroalkyl phosphates, polyhexafluoropropylene oxides; perfluoropolyethers; amino acids; N-acylamino acids or salts thereof; lecithin, isopropyl triisostearyl titanate, isostearyl sebacate, and mixtures thereof.

The term "alkyl" mentioned in the compounds cited above especially denotes an alkyl group containing from 1 to 30 carbon atoms and preferably containing from 5 to 16 carbon atoms.

Fillers

For the purposes of the present invention, the term "fillers" should be understood as meaning colourless or white solid particles of any form, which are in an insoluble and dispersed form in the medium of the composition.

These fillers, of mineral or organic, natural or synthetic nature, give the composition containing them softness and give the makeup result a matte effect and uniformity.

Preferably, a composition of the invention comprises fillers, particularly when it is dedicated to provide a high coverage.

In particular, a composition according to the invention may comprise from 2% to 35% by weight, especially from 5% to 35% by weight, in particular from 5% to 20% by weight of fillers relative to the total weight of the said composition.

According to one embodiment of the invention, a composition may comprise solid particles such as pigments and/or fillers.

Advantageously, a composition according to the invention may comprise from 0.01% to 25% by weight, especially from 0.1% to 25% by weight, in particular from 1% to 20% by weight and preferably from 5% to 15% by weight of solid particles relative to the total weight of the said composition.

Preferably, when a composition according to the invention is a make-up composition, it may comprise at least 5%, and more preferably at least 10% by weight of solid particles relative to the total weight of the said composition.

Dispersant

Advantageously, a composition according to the invention may also comprise a dispersant.

Such a dispersant may be a surfactant, an oligomer, a polymer or a mixture of several thereof.

According to one particular embodiment, a dispersant in accordance with the invention is a surfactant.

Active Agents

For a particular care application, a composition according to the invention may comprise at least one moisturizer (also known as a humectant).

Preferably, such moisturizer is glycerol.

The moisturizer(s) could be present in the composition in a content ranging from 0.1% to 15% by weight, especially from 0.5% to 10% by weight or even from 1% to 6% by weight, relative to the total weight of said composition.

As other active agents that may be used in the composition of the invention, examples that may be mentioned include vitamins and sunscreens, and mixtures thereof. Preferably, a composition of the invention comprises at least one active agent.

It is a matter of routine for those skilled in the art to adjust the nature and amount of the additives present in the compositions in accordance with the invention such that the desired cosmetic properties thereof are not thereby affected.

According to one embodiment, a composition of the invention may advantageously be in the form of a foundation.

According to one embodiment, a composition of the invention may advantageously be in the form of a composition for making up the skin and especially the face. It may thus be an eyeshadow or a face powder.

According to another embodiment, a composition of the invention may advantageously be in the form of a lip product, in particular a lipstick.

According to another embodiment, a composition of the invention may advantageously be in the form of a composition for caring for the skin of the body or the face, in particular the face.

According to another embodiment, a composition of the invention may be in the form of a product for the eyelashes, in particular a mascara.

Such compositions are especially prepared according to the general knowledge of a person skilled in the art.

Throughout the description, including the claims, the term "comprising a" should be understood as being synonymous with "comprising at least one", unless otherwise specified.

The expressions "between . . . and . . . " and "ranging from . . . to . . . " should be understood as meaning limits included, unless otherwise specified.

The invention is illustrated in greater detail by the examples and figures presented below. Unless otherwise mentioned, the amounts indicated are expressed as weight percentages.

Methodology for the Oscillating Dynamic Rheology Measurements

These are rheological measurements in the harmonic regime, which measure the elastic modulus.

The measurements are taken using a Haake RS600 rheometer on a product at rest, at 25° C. with a plate-plate rotor Ø 60 mm and a 2 mm gap.

The measurements in the harmonic regime make it possible to characterize the viscoelastic properties of the products. The technique consists in subjecting a material to a stress that varies sinusoidally over time and in measuring the response of the material to this stress. In a region in which the behaviour is linearly viscoelastic (zone in which the strain is proportional to the stress), the stress ($\tau$) and the strain ($\gamma$) are two sinusoidal functions of time that are written in the following manner:

$$\tau(t)=\tau_0 \sin(\omega t)$$

$$\gamma(t)=\gamma_0 \sin(\omega t+\delta)$$

in which:
$\tau_0$ represents the maximum amplitude of the stress (Pa);
$\gamma_0$ represents the maximum amplitude of the strain (-);
$\omega=2\Pi N$ represents the angular frequency (rad.s$^{-1}$) with N representing the frequency (Hz); and
$\delta$ represents the phase angle of the stress relative to the strain (rad).

Thus, the two functions have the same angular frequency, but they are dephased by an angle $\delta$. According to the phase angle $\delta$ between $\tau(t)$ and $\gamma(t)$, the behaviour of the system may be assessed:
 if $\delta=0$, the material is purely elastic;
 if $\delta=\Pi/2$, the material is purely viscous (Newtonian fluid); and
 if $0<\delta<\Pi/2$, the material is viscoelastic.

In general, the stress and the strain are written in complex form:

$$\tau^*(t)=\tau_0 e^{i\omega t}$$

$$\gamma^*(t)=\gamma_0 e^{i(\omega t+\delta)}$$

A complex stiffness modulus, representing the overall resistance of the material to the strain, whether it is of elastic or viscous origin, is then defined by:

$$G^*=\tau^*/\gamma^*=G'+iG''$$

in which:
G' is the storage modulus or elastic modulus, which characterizes the energy stored and totally restituted in the course of a cycle, $G'=(\tau_0/\gamma_0) \cos \delta$; and
G'' is the loss modulus or viscous modulus, which characterizes the energy dissipated by internal friction in the course of a cycle, $G''=(\tau_0/\gamma_0) \sin \delta$.

The parameter retained is the mean stiffness modulus G* recorded at the plateau measured at a frequency of 1 Hz.

EXAMPLE 1

Foundation formulations in accordance with the invention are prepared from the phases described below.
1) Preparation of the Aqueous Phases
The aqueous phases are prepared from the compounds that follow in the weight proportions stated in the tables below.
Phase A1:
Phase A1 gives freshness and lightness.

| Compounds | Weight % Phase A1 |
|---|---|
| Water | qs 100 |
| Glycerol | 10.00 |
| Butylene glycol | 6.25 |
| Phenoxyethanol | 0.63 |
| Caprylyl glycol | 0.63 |
| Hydroxyethyl acrylate/sodium acryloyldimethyltaurate copolymer (Sepinov ® EMT 10 sold by the company SEPPIC) | 1.7 |

The water, glycerol, butylene glycol, phenoxyethanol and caprylyl glycol are weighed out in a beaker and stirred using a Rayneri blender at room temperature.

The hydroxyethyl acrylate/sodium acryloyldimethyltaurate copolymer is added with stirring at room temperature. The stirring is adjusted so as not to incorporate air into the mixture.

The mixture is stirred moderately for about 10 minutes at room temperature.

Phase A2:

| Compounds | Weight % Phase A2 |
|---|---|
| Water | qs 100 |
| Glycerol | 8.19 |
| Caprylyl glycol | 0.50 |
| Phenoxyethanol | 0.50 |
| Yellow iron oxide | 1.77 |
| Red iron oxide | 0.52 |
| Black iron oxide | 0.08 |
| Titanium dioxide | 11.66 |
| Sodium polyacrylate (Cosmedia ® SP sold by the company BASF) | 0.70 |

The pigments are ground in 10% of the aqueous phase with the glycerol.

The other elements are weighed out in a beaker, the ground material is added thereto and the mixture is then stirred with a Rayneri blender at room temperature.

The sodium polyacrylate is added with stirring at room temperature. The stirring is adjusted so as not to incorporate air into the mixture.

The mixture is stirred moderately for about 10 minutes at room temperature.

Phase A3:

| Compounds | Weight % Phase A3 |
|---|---|
| Water | qs 100 |
| Glycerol | 8.19 |
| Caprylyl glycol | 0.50 |
| Phenoxyethanol | 0.50 |
| Yellow iron oxide | 1.77 |
| Red iron oxide | 0.52 |
| Black iron oxide | 0.08 |
| Titanium dioxide | 11.66 |
| Ammonium polyacryloyldimethyltaurate (Hostacerin AMPS ® sold by the company Clariant) | 1.70 |

The pigments are ground in 10% of the aqueous phase with the glycerol.

The other elements are weighed out in a beaker, the ground material is added thereto and the mixture is then stirred with a Rayneri blender at room temperature.

The ammonium polyacryloyldimethyltaurate is added with stirring at room temperature. The stirring is adjusted so as not to incorporate air into the mixture.

The mixture is stirred moderately for about 10 minutes at room temperature.

2) Preparation of the Oily Phases

The oily phases are prepared from the compounds that follow in the weight proportions stated in the tables below.

Phase B1:

| Compounds | Weight % Phase B1 |
|---|---|
| Dimethicone | qs 100 |
| 84.5% Dimethicone/15.5% Dimethicone Crosspolymer (DC9041 ® sold by the company Dow Corning) (*% of dimethicone crosspolymer solids) | 86 (13.33*) |

The oil is introduced into a beaker and stirred with a Rayneri blender at room temperature.

The gel of silicone elastomer in dimethicone is added with moderate stirring at room temperature.

The gel slowly thickens.

The mixture is stirred for 20 minutes.

Phase B2:

| Compounds | Weight % Phase B2 |
|---|---|
| Yellow iron oxide | 4.92 |
| Red iron oxide | 1.00 |
| Black iron oxide | 0.35 |
| Titanium dioxide | 11.24 |
| Dimethicone | qs 100 |
| 84.5% Dimethicone/15.5% Dimethicone Crosspolymer (DC9041 ® sold by the company Dow Corning) (*% of dimethicone crosspolymer solids) | 45 (6.98*) |

The pigments are ground with 15% of the silicone oil using a three-roll mill.

The ground material and the remainder of the oil are placed in a beaker and stirred with a Rayneri blender at room temperature.

The gel of silicone elastomer in dimethicone is added with moderate stirring at room temperature.

The gel slowly thickens.

The mixture is stirred for 20 minutes.

Phase B3:

| Compounds | Weight % Phase B3 |
|---|---|
| Yellow iron oxide | 4.92 |
| Red iron oxide | 1.00 |
| Black iron oxide | 0.35 |
| Titanium dioxide | 31.24 |
| Isononyl isononanoate | qs 100 |
| Bentone gel (Bentone Gel ISD V ® sold by the company Elementis (87% isododecane/10% disteardimonium hectorite/3% Propylene carbonate) (*% of disteardimonium hectorite solids) | 35.00 (*3.50) |

The pigments are ground with 15% of the ester using a three-roll mill.

The ground material and the remainder of the oil are placed in a beaker and stirred with a Rayneri blender at room temperature.

The gel of bentone in isododecane is added and the mixture is then stirred moderately for 20 minutes, during which time the gel slowly thickens at room temperature.

Phase B4:

| Compounds | Weight % Phase B4 |
|---|---|
| Yellow iron oxide | 4.92 |
| Red iron oxide | 1.00 |
| Black iron oxide | 0.35 |
| Titanium dioxide | 31.24 |
| Isononyl isononanoate | qs 100 |
| C30-45 alkyldimethylsilyl polypropylsilsesquioxane (SW-8005 ® C30 Resin Wax sold by the company Dow Corning) | 7.48 |
| Dextrin palmitate (Rheopearl ® KL2 sold by the company Chiba Flour Milling) | 2.44 |

The pigments are ground with 15% of the ester using a three-roll mill.

The ground material and the remainder of the oil are placed in a beaker and stirred with a Rayneri blender at room temperature.

The wax and the dextrin palmitate are added.

The mixture is heated at 95° C. for 25 to 30 minutes.

The mixture is allowed to cool to room temperature.

3) Preparation of Foundation Formulations

These formulations are obtained by mixing several phases intended to form the foundations in accordance with the invention, in the proportions described below in Table 1.

The aqueous and oily gels are weighed out and then mixed with a Rayneri blender.

The phases comprising waxes/fatty alcohols are destructured by stirring or using a three-roll mill before mixing.

The combination of the various phases is established as a function of the desired performance qualities.

TABLE 1

| Formulations | Technical performance quality(ies) obtained | Weight % Phase A1 | Weight % Phase A2 | Weight % Phase A3 | Weight % Phase B1 | Weight % Phase B2 | Weight % Phase B3 | Weight % Phase B4 |
|---|---|---|---|---|---|---|---|---|
| Formulation 1 | Freshness and velvety appearance | 80.00 | | | | 20.00 | | |
| Formulation 2 | Freshness and coverage | 60.00 | | | | 40.00 | | |
| Formulation 3 | Velvety appearance | 50.00 | | | | 50.00 | | |
| Formulation 4 | Freshness | 60.00 | | | | | 40.00 | |
| Formulation 5 | Comfort | 60.00 | | | | | | 40.00 |

TABLE 1-continued

| Formulations | Technical performance quality(ies) obtained | Weight % Phase A1 | Weight % Phase A2 | Weight % Phase A3 | Weight % Phase B1 | Weight % Phase B2 | Weight % Phase B3 | Weight % Phase B4 |
|---|---|---|---|---|---|---|---|---|
| Formulation 6 | Freshness and softness | | | 80.00 | 20.00 | | | |
| Formulation 7 | Freshness and softness | | 80.00 | | 20.00 | | | |

Formulation 1 is a gel of smooth and uniform appearance. The formulation penetrates quickly into the skin, and is fresh, light and easy to spread. It is neither greasy nor tacky, and has a matte finish. The composition is stable over time, at all temperatures.

Formulation 2 is creamy and light on application. The skin finish is soft and powdery. The makeup result is matte and covering. The aqueous gel, present in a proportion of 60%, conveys the lightness of the formulation.

EXAMPLE 2

A gloss formulation in accordance with the invention is prepared from the phases described below.

1) Preparation of the Aqueous Phase A1

The aqueous phase is prepared as mentioned in Example 1.

2) Preparation of the Oily Phase B5

The oily phase is prepared from the compounds that follow in the weight proportions stated in the table below.

Phase B5:

| Compounds | Weight % Phase B5 |
|---|---|
| Octyldodecanol | qs 100 |
| Phenyl trimethicone | 6.36 |
| Diisostearyl malate | 19.30 |
| Pentaerythrityl tetraisostearate | 15.46 |
| C18-36 acid triglyceride | 1.02 |
| Bis-diglyceryl polyacyladipate-2 | 14.20 |
| BHT | 0.08 |
| *Simmondsia chinensis* (jojoba) butter | 2.55 |
| Polyethylene (Asensa ® SC 211 sold by the company Honeywell) | 6.40 |
| Hydrogenated polyethylene cocoylglycerides (Softisan ® 100 sold by the company Cremer Oleo) | 5.00 |
| Microcrystalline wax (Cerewax ® No. 3 sold by the company Baerlocher) | 2.70 |
| Fragrance | 0.30 |
| Titanium dioxide | 1.65 |
| Iron oxides | 1.06 |
| Red 7 | 0.20 |
| Blue 1 lake | 0.17 |
| Yellow 6 lake | 0.00 |
| Mica (and) titanium dioxide (and) iron oxides | 0.50 |

The pigments are ground in the octyldodecanol using a three-roll mill.

The ground material and the other elements are placed in a beaker and stirred with a Rayneri blender at 95° C. for 25 to 30 minutes.

The mixture is allowed to cool to room temperature.

3) Preparation of the Gloss Formulation

This formulation is obtained by mixing the phases A1 and B5 intended to form the gloss in accordance with the invention, in the proportions described below in Table 2.

TABLE 2

| Formula | Weight % Phase A1 | Weight % Phase B5 |
|---|---|---|
| Formulation 8: Gloss | 50.00 | 50.00 |

The product obtained is a shiny, fresh gloss, which deposits a very thin pigmented film on the lips.

EXAMPLE 3

Care formulations in accordance with the invention are prepared from the phases described below.

1) Preparation of the Aqueous Phase A4

The aqueous phase A4 is prepared from the compounds that follow in the weight proportions stated in the table below.

Phase A4:

| Compounds | Weight % Phase A4 |
|---|---|
| Ammonium polyacryloyldimethyltaurate (Hostacerin AMPS ® sold by the company Clariant) | 1.3 |
| Caprylyl glycol | 0.5 |
| Dimethicone/vinyl dimethicone crosspolymer as a 63 percent suspension in water (BY29119 ® sold by the company Dow Corning) | 8.67 |
| Glycerol | 13 |
| Propylene glycol | 8.67 |
| Water | qs 100 |
| Crosslinked polyacrylate microspheres (Aquakeep ® 10 SH NF sold by the company Sumitomo Seika) | 0.33 |
| Phenoxyethanol | 0.5 |

Phase A4 is obtained by mixing at room temperature all the constituents described in the above table except for the crosslinked polyacrylate microspheres and the dimethicone/vinyl dimethicone solution.

After total dissolution of the constituents in the water, the crosslinked polyacrylate microspheres and the aqueous solution of dimethicone/vinyl dimethicone are then added to the mixture.

2) Preparation of the Oily Phase B6

The oily phase is prepared from the compounds that follow in the weight proportions stated in the table below.

Phase B6:

| Compounds | Weight % Phase B6 |
|---|---|
| Silica silylate (VM-2270 ® sold by the company Dow Corning) | 5.18 |
| 84.5% Dimethicone/15.5% Dimethicone Crosspolymer (DC9041 ®) sold by the company Dow Corning) (*% of dimethicone crosspolymer solids) | 33.09 (5.13*) |

-continued

| Compounds | Weight % Phase B6 |
|---|---|
| Acrylate copolymer (Expancel ® sold by the company Akzo Nobel) | 0.33 |
| Isostearyl neopentanoate | 36.29 |
| Isononyl isononanoate | 1.75 |
| Hydrogenated polyisobutene | qs 100 |
| Pentaerythrityl tetraethylhexanoate | 3.24 |

Phase B6 is obtained by mixing in a mixer of kneader type, at room temperature, all of the constituents described in the above table in the weight proportions specified therein, until a homogeneous gel is obtained.

3) Preparation of the Care Formulations 9, 10 and 11

These formulations are obtained by mixing phases A4 and B6 at room temperature in a Kenwood Chef mechanical kneader equipped with a stirrer of flexible anchor type, in the proportions indicated below in Table 3.

TABLE 3

| Formulations | Weight % Phase A4 | Weight % Phase B6 |
|---|---|---|
| Formulation 9 | 75.00 | 25.00 |
| Formulation 10 | 58.00 | 42.00 |
| Formulation 11 | 40.00 | 60.00 |

Compositions 9 to 11 have properties of smoothing the microrelief via optical effects.

4) Characterization of the Optical Properties

The optical properties of phases A4 and B6 and of formulations 9, 10 and 11 were characterized using the haze measurement (veil or mask effect) with a commercial "Hazemeter" machine.

The measurements were taken according to the following protocol: on a transparent plastic film (Byk), a layer with a wet thickness of 30 µm of the composition whose Haze it is desired to evaluate is spread, using an automatic spreader. It is left to dry for 24 hours in an oven at 30° C., and the haze index is then measured using a Byk Gardner brand Haze Gard machine.

The values obtained for phases A4 and B6 are as follows:

| Phases | Measured haze |
|---|---|
| Phase A4 | 46 |
| Phase B6 | 93 |

The haze values measured for formulations 9, 10 and 11 are given in the following table, along with the theoretical values calculated on the basis of the ratios of the phases A4 and B6 (for example, the theoretical haze for formulation 9 is calculated in the following manner: 0.75×46+0.25×93).

| Formulations | Measured haze | Theoretical haze |
|---|---|---|
| Formulation 11 | 82 | 74.2 |
| Formulation 10 | 81 | 65.8 |
| Formulation 9 | 88 | 57 |

Irrespective of the composition, the measured haze value is consistently greater than the theoretical value predicted by the ratio of the phases in the sample.

Consequently, the compositions according to the invention show proof of a real synergistic effect.

EXAMPLE 4

Care formulations in accordance with the invention are prepared from the phases described below.

1) Preparation of the Aqueous Phase A1, A5 and A6

The aqueous phase A1 is prepared as mentioned in Example 1.

The aqueous phases A5 and A6 are prepared from the compounds that follow in the weight proportions stated in the table below.

Phase A5:

| Compounds | Weight % Phase A5 |
|---|---|
| Water | qs 100 |
| Glycerol | 10 |
| Caprylyl glycol | 0.63 |
| Phenoxyethanol | 0.63 |
| Ammonium polyacryloyldimethyltaurate (Hostacerin AMPS ® sold by the company Clariant) | 1.70 |

The elements are weighed out in a beaker and the mixture is then stirred with a Rayneri blender at room temperature.

The ammonium polyacryloyldimethyltaurate is added with stirring at room temperature. The stirring is adjusted so as not to incorporate air into the mixture. The mixture is stirred moderately for about 10 minutes at room temperature.

Phase A6:

| Compounds | Weight % Phase A6 |
|---|---|
| Water | qs 100 |
| Glycerol | 10 |
| Caprylyl glycol | 0.63 |
| Phenoxyethanol | 0.63 |
| Sodium polyacrylate (Cosmedia ® SP sold by the company BASF) | 0.70 |

The elements are weighed out in a beaker and the mixture is then stirred with a Rayneri blender at room temperature.

The sodium polyacrylate is added with stirring at room temperature. The stirring is adjusted so as not to incorporate air into the mixture.

The mixture is stirred moderately for about 10 minutes at room temperature.

2) Preparation of the Oily Phase B7 and B8

The oily phase is prepared from the compounds that follow in the weight proportions stated in the table below.

Phase B7:

| Compounds | Weight % Phase B7 |
|---|---|
| Bentone gel (Bentone Gel ISD V ® sold by the company Elementis (87% isododecane/10% disteardimonium hectorite/ 3% Propylene carbonate) | 100 (*10) |
| (*% of disteardimonium hectorite solids) | |

Phase B8:

| Compounds | Weight % Phase B8 |
|---|---|
| 84.5% Dimethicone/15.5% Dimethicone Crosspolymer (DC9041 ® sold by the company Dow Corning) (*% of dimethicone crosspolymer solids) | 100 (*15.5) |

3) Preparation of the Care Formulations 12, 13, 14, 15, 16 and 17

These formulations are obtained by mixing phases A1, A5 or A6 with B7 or B8 at room temperature in a Kenwood Chef mechanical kneader equipped with a stirrer of flexible anchor type, in the proportions indicated below in Table 4.

TABLE 4

| Formulations | Weight % Phase A1 | Weight % Phase A5 | Weight % Phase A6 | Weight % Phase B7 | Weight % Phase B8 |
|---|---|---|---|---|---|
| Formulation 12 | 50 | | | 50 | |
| Formulation 13 | | 50 | | 50 | |
| Formulation 14 | | | 50 | 50 | |
| Formulation 15 | 50 | | | | 50 |
| Formulation 16 | | 50 | | | 50 |
| Formulation 17 | | | 50 | | 50 |

Compositions 12 to 17 have properties of smoothing the microrelief via optical effects.

4) Characterization of the Optical Properties

The optical properties of phases A1, A5, A6, B7 and B8 and of formulations 12 to 17 were characterized using the haze measurement (veil or mask effect) with a commercial "Hazemeter" machine.

The measurements were taken according to the following protocol detailed in example 3.

The values obtained for phases A1, A5, A6, B7 and B8 are as follows:

| Phases | Measured haze |
|---|---|
| Phase A1 | 1.1 |
| Phase A5 | 1.4 |
| Phase A6 | 23.9 |
| Phase B7 | 63.9 |
| Phase B8 | 70.4 |

The haze values measured for formulations 12 to 17 are given in the following table, along with the theoretical values calculated on the basis of the ratios of the phases A1, A5, A6, B7 and B8 (for example, the theoretical haze for formulation 12 is calculated in the following manner: 0.5× 1.1+0.5×63.9).

| Formulations | Measured haze | Theoretical haze |
|---|---|---|
| Formulation 12 | 72.3 | 32.5 |
| Formulation 13 | 65.3 | 32.7 |
| Formulation 14 | 69.3 | 43.9 |
| Formulation 15 | 64 | 35.8 |
| Formulation 16 | 66 | 35.9 |
| Formulation 17 | 59.1 | 47.2 |

Irrespective of the composition, the measured haze value is consistently greater than the theoretical value predicted by the ratio of the phases in the sample.

Consequently, the compositions according to the invention show proof of a real synergistic effect.

EXAMPLE 5

A self-smoothing foundation in accordance with the invention is prepared from the phases described below.

1) Preparation of the Aqueous Phase A7

Phase A7:

| Phases | Compounds | Weight % Phase A7 |
|---|---|---|
| (1) | Water | Qs 100 |
| | Glycerol | 3 |
| | Propylene glycol | 2 |
| | Preservatives | 0.9 |
| | Tetrasodium EDTA | 0.1 |
| (2) | Steareth-100/PEG-136/HDI Copolymer (Rheolate FX1100 sold by the company Elementis) | 1.5 |
| | Water | 23.5 |
| (3) | Acrylates/C10-30 Alkyl acrylate crosspolymer (Pemulen TR-2 sold by the company Lubrizol) | 0.2 |
| | Water | 10 |
| (4) | Sodium hydroxide | 0.04 |

The water of phase (2) is weighed and moderately stirred with a Rayneri blender. The polymer of phase (2) is weighed in a capsule and slowly added in water under stirring.

The phase (2) is allowed to stand during 24 hours at 4° C.

The water of phase (3) is weighed and moderately stirred with a Rayneri blender. The polymer of phase (2) is weighed in a capsule and slowly added in water under stirring.

The elements of phase (1), except water, are weighed out in a beaker. The water is then poured at 80° C. on the elements of phase (1) and moderately stirred with a Rayneri blender.

When the temperature of the mixture (1) is lower than 40° C., the phase (2) is poured under moderate stirring. The mixture is allowed to stand during 5 minutes to homogenize it. The phase (3) is then poured on the mixture under moderate stirring and then neutralize with phase (4). The mixture is allowed to stand during 5 minutes to homogenize it.

2) Preparation of the Oily Phase B9

The oily phase is prepared from the compounds that follow in the weight proportions stated in the table below.

Phase B9:

| Compounds | Weight % Phase B9 |
|---|---|
| Yellow iron oxide coated with aluminium stearoyl glutamate (NAI sold by the company MIYOSHI KASEI) | 4.92 |
| Red iron oxide coated with aluminium stearoyl glutamate (NAI sold by the company MIYOSHI KASEI) | 1.00 |
| Black iron oxide coated with aluminium stearoyl glutamate (NAI sold by the company MIYOSHI KASEI) | 0.35 |
| Titanium dioxide coated with aluminium stearoyl glutamate | 31.24 |

-continued

| Compounds | Weight % Phase B9 |
|---|---|
| (NAI sold by the company MIYOSHI KASEI) | |
| Isononyl isononanoate | qs 100 |
| Bentone gel (Bentone Gel ISD V ® sold by the company Elementis (87% isododecane/10% disteardimonium hectorite/3% Propylene carbonate) (*% of disteardimonium hectorite solids) | 35.00 (*3.50) |

The pigments are ground with 15% of the ester using a three-roll mill.

The ground material and the remainder of the oil are placed in a beaker and stirred with a Rayneri blender at room temperature.

The gel of bentone in isododecane is added and the mixture is then stirred moderately for 20 minutes, during which time the gel slowly thickens at room temperature.

3) Preparation of the Self-Smoothing Formulation

This formulation is obtained by mixing the phases A7 and B9 intended to form the formulation in accordance with the invention, in the proportions described below in Table 5.

TABLE 5

| Formula | Weight % Phase A7 | Weight % Phase B9 |
|---|---|---|
| Formulation 18: Self-smoothing | 90.00 | 10.00 |

The product obtained has a smooth aspect and a shiny mirror-type appearance. The composition has self-smoothing properties. The application of the formulation is easy and the deposit is fresh, light and homogeneous.

The make-up result is natural, non-sticky and thin.

EXAMPLE 6

A gel foundation formulation in accordance with the invention is prepared from the phases described below.

1) Preparation of the Aqueous Phase A8

Phase A8:

| Phases | Compounds | Weight % Phase A8 |
|---|---|---|
| (1) | Water | Qs 100 |
| | Glycerol | 10 |
| | Butylene glycol | 6.25 |
| | Preservatives | 1.25 |
| | Tetrasodium EDTA | 0.1 |
| (2) | Hydroxyethyl acrylate/sodium acryloyldimethyltaurate copolymer (Sepinov ® EMT 10 sold by the company SEPPIC) | 2.16 |
| | Steareth-100/PEG-136/HDI Copolymer (Rheolate FX1100 sold by the company Elementis) | 0.88 |

The elements of phase (1) are weighed out in a beaker and moderately stirred with a Rayneri blender.

The polymers of phase (2) are weighed and slowly sprinkled on the mixture of phase (1) under stirring. The stirring is adjusted by increasing the speed gradually as the gel thickens. After the incorporation of the gelling agents, the mixture is allowed to stand during 10 minutes to homogenize it.

2) Preparation of the Oily Phase B10

The oily phase is prepared from the compounds that follow in the weight proportions stated in the table below.

Phase B10:

| Compounds | Weight % Phase B10 |
|---|---|
| Yellow iron oxide coated with aluminium stearoyl glutamate (NAI sold by the company MIYOSHI KASEI) | 4.92 |
| Red iron oxide coated with aluminium stearoyl glutamate (NAI sold by the company MIYOSHI KASEI) | 1.00 |
| Black iron oxide coated with aluminium stearoyl glutamate (NAI sold by the company MIYOSHI KASEI) | 0.35 |
| Titanium dioxide coated with aluminium stearoyl glutamate (NAI sold by the company MIYOSHI KASEI) | 31.24 |
| Dimethicone (Xiameter PMX-200 silicone fluid 5CS by Dow Corning) | qs 100 |
| 84.5% Dimethicone/15.5% Dimethicone Crosspolymer (DC9041 ® sold by the company Dow Corning) (*% of dimethicone crosspolymer solids) | 45.00 (*6.98) |

The pigments are ground with 15% of the silicone oil using a three-roll mill.

The ground material and the remainder of the oil are placed in a beaker and stirred with a Rayneri blender at room temperature.

The gel of silicone elastomer in dimethicone is added with moderate stirring at room temperature.

The gel slowly thickens.

The mixture is stirred for 20 minutes.

3) Preparation of the Gel Foundation Formulation

This formulation is obtained by mixing the phases A8 and B10 intended to form the formulation in accordance with the invention, in the proportions described below in Table 6.

TABLE 6

| Formula | Weight % Phase A8 | Weight % Phase B10 |
|---|---|---|
| Formulation 19: gel Foundation | 80.00 | 20.00 |

The obtained gel foundation is dense and elastic during the grip of the composition. The application is both fresh and comfortable. The make-up result is natural, matte, smooth and homogeneous.

EXAMPLE 7

A blush formulation in accordance with the invention is prepared from the phases described below.

1) Preparation of the Aqueous Phase A9

Phase A9:

| Phases | Compounds | Weight % Phase A9 |
|---|---|---|
| (1) | Water | Qs 100 |
| | Glycerol | 10.17 |
| | Butylene glycol | 6.36 |
| | Preservatives | 1 |
| (2) | Hydroxyethyl acrylate/sodium acryloyldimethyltaurate copolymer (Sepinov ® EMT 10 sold by the company SEPPIC) | 2.23 |
| | Steareth-100/PEG-136/HDI Copolymer (Rheolate FX1100 sold by the company Elementis) | 0.94 |

The elements of phase (1) are weighed out in a beaker and moderately stirred with a Rayneri blender.

The polymers of phase (2) are weighed and slowly sprinkled on the mixture of phase (1) under stirring. The stirring is adjusted by increasing the speed gradually as the gel thickens. After the incorporation of the gelling agents, the mixture is allowed to stand during 10 minutes to homogenize it.

2) Preparation of the Oily Phase B11

The oily phase is prepared from the compounds that follow in the weight proportions stated in the table below.

Phase B11:

| Phases | Compounds | Weight % Phase B11 |
| --- | --- | --- |
| (1) | Dimethicone (Xiameter PMX-200 silicone fluid 5CS by Dow Corning) | qs 100 |
| | 84.5% Dimethicone/15.5% Dimethicone Crosspolymer (DC9041 ® sold by the company Dow Corning) (*% of dimethicone crosspolymer solids) | 65.25 (*10.11) |
| (2) | Mica (and) barium sulfate (and) titanium dioxide (Ronaflair low luster pigment sold by the company Merck) | 6.71 |
| | Mica (and) titanium dioxide (and) Red 6 (and) Tin oxide (Intenza mango tango C91-1221 sold by the company Sun) | 2.68 |
| | Red 21 (Suncroma D&C Red 21 C14-032 sold by the company Sun) | 0.01 |

The gel of silicone elastomer in dimethicone is added and moderately stirred with a Rayneri blender and the dimethicone is added under moderate stirring at room temperature.

The gel slowly thickens.

The mixture is stirred for 20 minutes.

3) Preparation of the Blush Formulation

This formulation is obtained by mixing the phases A9 and B11 intended to form the formulation in accordance with the invention, in the proportions described below in Table 7.

TABLE 7

| Formula | Weight % Phase A9 | Weight % Phase B11 |
| --- | --- | --- |
| Formulation 20: Blush | 85.00 | 15.00 |

The obtained blush is very fresh and easy to apply on skin. The result is smooth and looks very natural. The skin finish is matte.

The invention claimed is:

1. Cosmetic composition for making up and/or caring for keratin materials comprising:
   at least one aqueous phase gelled with at least one synthetic polymeric hydrophilic gelling agent; and
   at least one oily phase gelled with at least one lipophilic gelling agent;
   the said phases forming therein a macroscopically homogeneous mixture,
   wherein the hydrophilic gelling agent(s)/lipophilic gelling agent(s) consists of a system selected from the group consisting of:
   copolymer of 2-acrylamido-2-methylpropanesulfonic acid and of hydroxyethyl acrylate/organopolysiloxane elastomer;
   polymer of 2-acrylamido-2-methylpropanesulfonic acid combined with a crosslinked sodium polyacrylate/hydrophobic silica combined with an organopolysiloxane elastomer;
   copolymer of 2-acrylamido-2-methylpropanesulfonic acid and of hydroxyethyl acrylate/modified clay;
   copolymer of 2-acrylamido-2-methylpropanesulfonic acid and of hydroxyethyl acrylate combined with an associative polyurethane/organopolysiloxane elastomer;
   copolymer of 2-acrylamido-2-methylpropanesulfonic acid and of hydroxyethyl acrylate/hydrophobic silica combined with an organopolysiloxane elastomer-polymer of 2-acrylamido-2-methylpropanesulfonic acid/organopolysiloxane elastomer; and
   polymer of 2-acrylamido-2-methylpropanesulfonic acid/modified clay.

2. Composition according to claim 1, containing at least one dyestuff.

3. Composition according to claim 1, in which the organopolysiloxane elastomer is selected from the group consisting of Dimethicone Crosspolymer, Dimethicone (and) Dimethicone Crosspolymer, Vinyl Dimethicone Crosspolymer, Dimethicone/Vinyl Dimethicone Crosspolymer and Dimethicone Crosspolymer-3.

4. Composition according to claim 1, containing the aqueous and oily phases in an aqueous phase/oily phase weight ratio of from 95/5 to 5/95.

5. Composition according to claim 1, which is in the form of a foundation, a face powder, an eyeshadow, a lipstick, a mascara and/or a care composition.

6. Composition according to claim 1, further comprising solid particles.

7. Composition according to claim 6, comprising from 0.01% to 25% by weight of solid particles relative to the total weight of the said composition.

8. Composition according to claim 1, further comprising volatile and/or non volatile silicone oils.

9. Composition according to claim 1, further comprising a moisturizer.

10. Composition according to claim 1, for making up and/or caring for the skin and/or the lips.

11. Composition according to claim 1, containing at least one dyestuff present at least in the gelled oily phase.

12. Composition according to claim 1, containing the aqueous and oily phases in an aqueous phase/oily phase weight ratio of from 60/40 to 70/30.

13. Composition according to claim 1, further comprising solid particles chosen from pigments and/or fillers.

14. Process for preparing a cosmetic composition for making up and/or caring for keratin materials, comprising at least one step of mixing:
   at least one aqueous phase gelled with at least one synthetic polymeric hydrophilic gelling agent; and
   at least one oily phase gelled with at least one lipophilic gelling agent;
   under conditions suitable for obtaining a macroscopically homogeneous mixture,
   wherein the hydrophilic gelling agent(s)/lipophilic gelling agent(s) consists of a system selected from the group consisting of:
   copolymer of 2-acrylamido-2-methylpropanesulfonic acid and of hydroxyethyl acrylate/organopolysiloxane elastomer;
   polymer of 2-acrylamido-2-methylpropanesulfonic acid combined with a crosslinked sodium polyacrylate/hydrophobic silica combined with an organopolysiloxane elastomer;
   copolymer of 2-acrylamido-2-methylpropanesulfonic acid and of hydroxyethyl acrylate/modified clay;

copolymer of 2-acrylamido-2-methylpropanesulfonic acid and of hydroxyethyl acrylate combined with an associative polyurethane/organopolysiloxane elastomer;

copolymer of 2-acrylamido-2-methylpropanesulfonic acid and of hydroxyethyl acrylate/hydrophobic silica combined with an organopolysiloxane elastomer-polymer of 2-acrylamido-2-methylpropanesulfonic acid/organopolysiloxane elastomer; and polymer of 2-acrylamido-2-methylpropanesulfonic acid/modified clay.

15. Process according to claim 14, comprising a step of mixing at least three or even more gelled phases.

16. Process according to claim 14, in which the mixing is performed at room temperature.

17. Cosmetic process for making up and/or caring for keratin materials, comprising at least one step which consists in applying to the said keratin material a cosmetic composition for making up and/or caring for keratin materials, comprising at least one aqueous phase gelled with at least one synthetic polymeric hydrophilic gelling agent; and at least one oily phase gelled with at least one lipophilic gelling agent; the said phases forming therein a macroscopically homogeneous mixture, wherein the hydrophilic gelling agent(s)/lipophilic gelling agent(s) consists of a system selected from the group consisting of:

copolymer of 2-acrylamido-2-methylpropanesulfonic acid and of hydroxyethyl acrylate/organopolysiloxane elastomer;

polymer of 2-acrylamido-2-methylpropanesulfonic acid combined with a crosslinked sodium polyacrylate/hydrophobic silica combined with an organopolysiloxane elastomer;

copolymer of 2-acrylamido-2-methylpropanesulfonic acid and of hydroxyethyl acrylate/modified clay;

copolymer of 2-acrylamido-2-methylpropanesulfonic acid and of hydroxyethyl acrylate combined with an associative polyurethane/organopolysiloxane elastomer;

copolymer of 2-acrylamido-2-methylpropanesulfonic acid and of hydroxyethyl acrylate/hydrophobic silica combined with an organopolysiloxane elastomer-polymer of 2-acrylamido-2-methylpropanesulfonic acid/organopolysiloxane elastomer; and polymer of 2-acrylamido-2-methylpropanesulfonic acid/modified clay.

18. Cosmetic process for making up and/or caring for a keratin material, comprising at least the application to the said material of a macroscopically homogeneous composition obtained by extemporaneous mixing, before application or at the time of application to the said keratin material, of (i) at least one aqueous phase gelled with at least one synthetic polymeric hydrophilic gelling agent, and (ii) at least one oily phase gelled with at least one lipophilic gelling agent, wherein the hydrophilic gelling agent(s)/lipophilic gelling agent(s) consists of a system selected from the group consisting of:

copolymer of 2-acrylamido-2-methylpropanesulfonic acid and of hydroxyethyl acrylate/organopolysiloxane elastomer;

polymer of 2-acrylamido-2-methylpropanesulfonic acid combined with a crosslinked sodium polyacrylate/hydrophobic silica combined with an organopolysiloxane elastomer;

copolymer of 2-acrylamido-2-methylpropanesulfonic acid and of hydroxyethyl acrylate/modified clay;

copolymer of 2-acrylamido-2-methylpropanesulfonic acid and of hydroxyethyl acrylate combined with an associative polyurethane/organopolysiloxane elastomer;

copolymer of 2-acrylamido-2-methylpropanesulfonic acid and of hydroxyethyl acrylate/hydrophobic silica combined with an organopolysiloxane elastomer-polymer of 2-acrylamido-2-methylpropanesulfonic acid/organopolysiloxane elastomer; and polymer of 2-acrylamido-2-methylpropanesulfonic acid/modified clay.

* * * * *